United States Patent [19]

Toki et al.

[11] Patent Number: 5,288,727
[45] Date of Patent: Feb. 22, 1994

[54] HYDRAZONE COMPOUNDS, PROCESSES FOR THEIR PRODUCTION, INTERMEDIATES USEFUL FOR THEIR PRODUCTION AND PESTICIDAL COMPOSITIONS CONTAINING THEM

[75] Inventors: Tadaaki Toki; Toru Koyanagi; Kiyomitsu Yoshida; Hiroshi Sasaki; Masayuki Morita; Tetsuo Yoneda, all of Kusatsu, Japan

[73] Assignee: Ishihara Sangyo Kaisha Ltd., Osaka, Japan

[21] Appl. No.: 834,835

[22] Filed: Feb. 13, 1992

[30] Foreign Application Priority Data

Feb. 22, 1991 [JP] Japan .................. 3-114191

[51] Int. Cl.$^5$ .............. C07C 251/80; C07C 251/88; A01N 47/40
[52] U.S. Cl. .................. 514/632; 514/478; 514/614; 514/639; 560/27; 564/151; 564/226; 564/249
[58] Field of Search ........... 564/249, 226, 151; 514/639, 632.1, 614, 478; 560/27

[56] References Cited

U.S. PATENT DOCUMENTS

| | | | |
|---|---|---|---|
| 3,732,307 | 5/1973 | Middleton | 564/251 |
| 4,145,444 | 3/1979 | Hamazaki et al. | |

FOREIGN PATENT DOCUMENTS

| | | |
|---|---|---|
| 0003913 | 9/1979 | European Pat. Off. |
| 0026040 | 4/1981 | European Pat. Off. |
| 0254461 | 1/1988 | European Pat. Off. |
| 0355832 | 2/1990 | European Pat. Off. |
| 0461483 | 12/1991 | European Pat. Off. |
| 50-16410 | 6/1975 | Japan |
| 1202170 | 8/1970 | United Kingdom |
| 1265052 | 3/1972 | United Kingdom |
| 2205838 | 12/1988 | United Kingdom |

OTHER PUBLICATIONS

Yuki Gosei Kagaku Kyokaishi, vol. 17, pp. 777-782, 1959, Teiichi ANDO, "Reactions of α-Halo Carbonyl Compounds With Gridnard Reagents, II".

Kogyo Kagaku Zaschi, vol. 72, No. 5, pp. 1107-1110, 1969.

Journal of Organic Chemistry, vol. 31, No. 2, pp. 624-625, Feb. 1966, R. J. Theis, et al., "The direct Synthesis of Phenylace-Tylenes from Monohydrazones".

Journal of Organic Chemistry, vol. 32, No. 5, pp. 1402-1409, May 1967, D. D. Jones, et al., "The Alkaline Hydrogen Peroxide Oxidation of Phenyl-2--Propanones$^{1a}$".

Journal of Organometallic Chemistry, vol. 179, pp. 301-309, 1979, C. H. Chao, et al., "Substituted Tetralin Formation from o-Palladated Schiff Bases and Two Equivanlents of Methyl Acrylate".

(List continued on next page.)

Primary Examiner—Allen J. Robinson
Assistant Examiner—Peter G. O'Sullivan
Attorney, Agent, or Firm—Oblon, Spivak, McClelland, Maier & Neustadt

[57] ABSTRACT

The present invention relates to a hydrazone compound of the formula (I) or its salt, a process for its preparation, an intermediate of the formula (II-5), a pesticidal composition containing said hydrazone compound or its salt as the active ingredient, and a pesticidal method of applying an effective amount thereof:

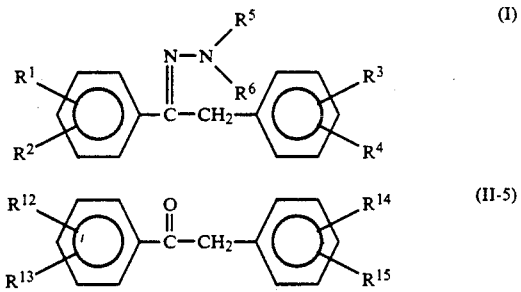

4 Claims, No Drawings

OTHER PUBLICATIONS

Journal of American Chemical Society, vol. 97, No. 25, pp. 7372-7374, 1975, C. E. Sacks, et al., "α-Arylation of Carbonyl Groups. Utilization of the p-Toluenesulfonylazo Olefin Functional Group as an Enolonium Synthon".

Journal of Chemical Society, pp. 4089-4092, 1957, R. L. Huang, "The Reaction of Phenacyl Halides with Grignard Reagents. A Synthesis of Dibenzyl Ketones and Deoxybenzoins".

Journal of Chemical Society, vol. 17, pp. 2165-2170, 1972, T. L. Gilchrist, et al., "The Reaction of 1,2,3-Thiadiazoles and 1,2,3-Selenadiazoles with Nona-Carbonyldi-Iron[1]".

Journal of Medical Chemistry, vol. 25, No. 9, pp. 1056-1060, 1982, P. C. Ruenitz et al., "Estrogenic and Antiestrogenic Activity of Monophenolic Analogues of Tamoxifen, Z-2-[p-1,2-Diphenyl-1-Bentenyl)Phenoxy]-N,N-Dimethylethylamine".

Jour. of Medicinal Chemistry, vol. 28, No. 4, pp. 442-446, 1985, E. W. Thomas, et al., "Synthesis and Platelet Aggregation Inhibitory Activity of 4,5-Bis (Substituted)-1,2,3-Thiadiazoles".

Chemical Berichte, vol. 113, No. 1, pp. 183-192, 1980, H. Meier, et al., "Umsetzung von Substituierten Hydrazonen mit Thionylchlorid und Sulfurylchlorid".

Journal of Indian Chemical Society, vol. 65, No. 8, pp. 564-566, Aug. 1988, Y. Joshi, et al., "[Diazotisation Rearrangement of Tosylhydrazones of Ortho-and Meta-Substituted-Benzophenones and α-Substituted-Acetophenones (Synthesis of Anilldes)".

Tetrahedron Letters, No. 3, pp. 171-174, 1976, H. Meier, et al., "Oxide der 1,2,3-Thiadiazone V[1]) Photolyse der 1,2,3-Thiadiazol-1,1,2-Trioxide".

Liebigs Ann. Chem., No., 8, pp. 1347-1353, 1977, G. Trickes, et al., "Photochemische Ringfragmentierung der 1,2,3-Thiadiazol-1,1,3-Trioxide".

Bull. Soc. Chim., pp. 395-399, 1960, R. Royer, et al., "II.-Degradation des Alcoyl-2 Acyl-3 Benzofurannes par la Soude (*)".

Bull. Inst. Chem., pp. 250-258, 1965, S. Kunichika, et al., "Syntheses of Dimethyldibenzyls".

HYDRAZONE COMPOUNDS, PROCESSES FOR THEIR PRODUCTION, INTERMEDIATES USEFUL FOR THEIR PRODUCTION AND PESTICIDAL COMPOSITIONS CONTAINING THEM

The present invention relates to hydrazone compounds, processes for their production, intermediates useful for their production, pesticidal compositions and pesticidal methods.

Hydrazone compounds are disclosed, for example, in Japanese Examined Patent Publication No. 16410/1975 and EP 3,913A, EP 26,040A, EP 254,461A and EP 355,832A. However, compounds of the present invention represented by the after-mentioned formula (I) are not disclosed in these references.

The present invention provides a hydrazone compound of the formula (I) or its salt:

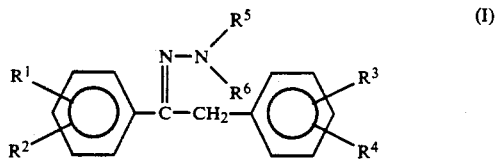

wherein each of $R^1$, $R^2$ and $R^4$, which are independent of one another, is a hydrogen atom, a halogen atom, a nitro group, a cyano group, a hydroxyl group, a trialkylsilyl group, an alkyl group which may be substituted, a cycloalkyl group which may be substituted, an alkoxy group which may be substituted, an alkylthio group which may be substituted, a carboxyl group which may be substituted, an aryl group which may be substituted, or an aryloxy group which may be substituted, $R^3$ is a hydrogen atom, a halogen atom, a nitro group, a cyano group, a hydroxyl group, an alkyl group which may be substituted, a cycloalkyl group which may be substituted, an alkoxy group which may be substituted, an alkylthio group which may be substituted, a carboxyl group which may be substituted, $X^1SO_2NH-$, $X^2CO_2-$, $X^3SO-$ $X^4SO_2-$, $X^5SO_3-$ or $(X^6Y^1)_2P(=Y^2)Y^3-$, and each of $R^5$ and $R^6$, which are independent of each other, is a hydrogen atom, an alkyl group which may be substituted, $X^7CO-$, $X^8OCO-$, $X^9SO_2-$, a carbamoyl group which may be substituted, an alkenyl group which may be substituted, an alkynyl group which may be substituted, or a heteroaryl group which may be substituted, or $R^5$ and $R^6$ together form $=CR^7R^8$, wherein each of $X^1$, $X^2$, $X^3$, $X^4$, $X^5$, $X^8$ and $X^9$, which are independent of one another, is an alkyl group which may be substituted, an alkoxy group which may be substituted, an alkenyl group which may be substituted, or an aryl group which may be substituted, $X^6$ is an alkyl group which may be substituted, an alkenyl group which may be substituted, or an aryl group which may be substituted, $X^7$ is a hydrogen atom, an alkyl group which may be substituted, an alkenyl group which may be substituted, or an aryl group which may be substituted, each of $Y^1$, $Y^2$ and $Y_3$, which are independent of one another, is an oxygen atom or a sulfur atom, and each of $R^7$ and $R^8$, which are independent of each other, is a hydrogen atom, an alkyl group which may be substituted, a cycloalkyl group which may be substituted, an alkoxy group which may be substituted, an alkenyl group which may be substituted, an aryl group which may be substituted, an amino group which may be substituted, or a cyclic amino group which may be substituted, provided that the following cases (1) to (10) are excluded:

(1) a case where $R^3$ and $R^4$ are simultaneously hydrogen atoms, (2) a case where at least one of $R^5$ and $R^6$ is an unsubstituted carbamoyl group, (3) a case where at least one of $R^1$, $R^2$, $R^3$ and $R^4$ is a nitro group, (4) a case where $R^2$, $R^4$ and $R^5$ are hydrogen atoms, $R^6$ is an ethoxycarbonyl group, and at least one of $R^1$ and $R^3$ is a p-methoxy group, (5) a case where $R^1$, $R^2$, $R^4$ and $R^5$ are hydrogen atoms, $R^3$ is a p-tert-butyl group, and $R^6$ is an ethoxycarbonyl group, (6) a case where $R^1$, $R^2$ and $R^4$ are hydrogen atoms, $R^3$ is a p-fluorine atom, $R^5$ is an isopropyl group, and $R^6$ is a hydrogen atom or an acetyl group, (7) a case where $R^1$, $R^2$, $R^4$, $R^5$ and $R^6$ are hydrogen atoms, and $R^3$ is a p-chlorine atom, (8) a case where $R^7$ is an unsubstituted phenyl group, and $R^8$ is a benzyl group which may be substituted, (9) a case where $R^1$, $R^2$ and $R^3$ are methoxy groups, $R^4$ is a hydrogen atom, and $R^5$ and $R^6$ are methyl groups, and

(10) a case where $R^5$ is a hydrogen atom, and $R^6$ is a phenylsulfonyl group which may be substituted, and a process for its production.

The present invention also provides an intermediate of the formula (II-5):

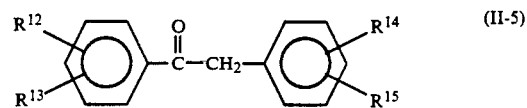

wherein each of $R^{12}$, $R^{13}$, $R^{14}$ and $R^{15}$, which are independent of one another, is a hydrogen atom, a halogen atom, or an alkyl group which may be substituted by a halogen atom, provided that the following cases (1) to (4) are excluded:

(1) a case where each of $R^{12}$, $R^{13}$, $R^{14}$ and $R^{15}$, which are independent of one another, is a hydrogen atoms or a halogen atom, (2) a case where $R^{12}$ or $R^{13}$ is a p-trifluoromethyl group, and $R^{14}$ or $R^{15}$ is a p-trifluoromethyl group, (3) a case where $R^{12}$ or $R^{13}$ is a halogen atom, and $R^{14}$ or $R^{15}$ is a methyl group, an ethyl group or a propyl group, and (4) a case where $R^{12}$ or $R^{13}$ is a methyl group, an ethyl group or a propyl group, and $R^{14}$ or $R^{15}$ is a halogen atom.

Further, the present invention provides a pesticidal composition comprising a pesticidally effective amount of a hydrazone compound of the formula (IX) or its salt:

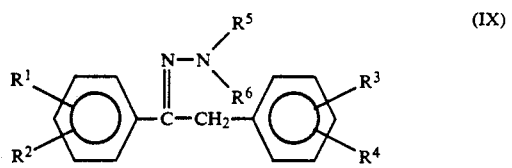

wherein $R^1$, $R^2$, $R^3$, $R^4$, $R^5$ and $R^6$ are as defined above, provided that a case where $R^3$ and $R^4$ are simultaneously hydrogen atoms, is excluded, and an agricultural adjuvant, and a pesticidal method which comprises applying to pests an effective amount of a hydrazone compound of the formula (IX) or its salt.

Now, the present invention will be described in detail with reference to the preferred embodiments.

The substituent for each of the alkyl group which may be substituted, the alkoxy group which may be substituted, the alkylthio group which may be substituted, the alkenyl group which may be substituted and the alkynyl group which may be substituted in the definitions of the formula (I) and (IX), may be a halogen atom; an alkoxy group which may be substituted by a halogen atom; a phenyl group which may be substituted by a halogen atom or by an alkyl group which may be substituted by a halogen atom; a phenoxy group which may be substituted by a halogen atom or by an alkyl group which may be substituted by a halogen atom; a cyano group; an alkylamino group; or an alkoxycarbonyl group, the carboxyl group which may be substituted, is a carboxyl group in which the hydrogen atom may be substituted by another substituent, and such another substituent may be an alkyl group which may be substituted by a halogen atom; or an aryl group which may be substituted by a halogen atom or by an alkyl group which may be substituted by a halogen atom, the substituent for each of the heteroaryl group which may be substituted, the aryl group which may be substituted, the aryloxy group which may be substituted and the cycloalkyl group which may be substituted, may be a halogen atom; an alkoxy group which may be substituted by a halogen atom; an alkyl group which may be substituted by a halogen atom; a phenyl group which may be substituted by a halogen atom or by an alkyl group which may be substituted by a halogen atom; a phenoxy group which may be substituted by a halogen atom or by an alkyl group which may be substituted by a halogen atom; a cyano group; an alkylamino group; or an alkoxycarbonyl group, and the substituent for each of the carbamoyl group which may be substituted, the amino group which may be substituted and the cyclic amino group which may be substituted, may be an alkoxy group which may be substituted by a halogen atom; an alkyl group which may be substituted by a halogen atom, a phenyl group which may be substituted by a halogen atom or by an alkyl group which may be substituted by a halogen atom; a phenoxy group which may be substituted by a halogen atom or by an alkyl group which may be substituted by a halogen atom; a cyano group; an alkylamino group; or an alkoxycarbonyl group.

The number of these substituents is one or more. Further the number of the halogen atom, the alkyl group, the alkyl group substituted by a halogen atom, and the halogen atom of alkyl group substituted by a halogen atom for these substitutents, is one or more.

In a case where the number of these substituents or radicals is two or more, such plural substituents or radicals may be the same or different.

In the definitions of the formulas (I), (II-5) and (IX), the alkyl group or the alkyl moiety may be a $C_{1-6}$ alkyl group such as a methyl group, an ethyl group, a propyl group, a butyl group, a pentyl group or a hexyl group, the alkenyl group or the alkenyl moiety may be a $C_{2-6}$ alkenyl group such as a vinyl group, a propenyl group, a butenyl group, a pentenyl group or a hexenyl group, and the alkynyl group or the alkynyl moiety may be a $C_{2-6}$ alkynyl group such as an ethynyl group, a propynyl group, a butynyl group, a pentynyl group or a hexynyl group.

Such respective groups and moieties include structural isomers of linear and branched aliphatic chains.

Further, the cycloalkyl group or the cycloalkyl moiety in the definitions of the formulas (I) and (IX), may be a $C_{3-6}$ cycloalkyl group such as a cyclopropyl group, a cyclobutyl group, a cyclopentyl group or a cyclohexyl group.

In the definitions of the formulas (I) and (IX), the aryl group may, for example, be a phenyl group or a naphthyl group, and the heteroaryl group may, for example, be a furyl group, a thienyl group or a pyridyl group.

The cyclic amino group in the definitions of the formulas (I) and (IX) may be $-N(CH_2)_n$ wherein n is an integer of from 2 to 7.

The halogen atom in the definitions of the formulas (I), (II-5) and (IX) may, for example, be a fluorine atom, a chlorine atom, a bromine atom or an iodine atom.

Preferred among the compounds of the formulas (I) and (IX) will be described.

(1) Each of $R^1$, $R^2$ and $R^4$, which are independent of one another, is preferably a hydrogen atom, a halogen atom, an alkyl group which may be substituted, an alkoxy group which may be substituted, an alkylthio group which may be substituted, or a carboxyl group which may be substituted, more preferably a hydrogen atom, a halogen atom, an alkyl group which may be substituted, or an alkoxy group which may be substituted, most preferably a hydrogen atom, a halogen atom, an alkyl group which may be substituted by a halogen atom, or an alkoxy group which may be substituted by a halogen atom.

(2) $R^3$ is preferably a halogen atom, an alkyl group which may be substituted, an alkoxy group which may be substituted, an alkylthio group which may be substituted, a carboxyl group which may be substituted, or $X^5SO_3-$ (wherein $X^5$ is an alkyl group which may be substituted), more preferably a halogen atom, an alkyl group which may be substituted, or an alkoxy group which may be substituted, most preferably a halogen atom, an alkyl group which may be substituted by a halogen atom, or an alkoxy group which may be substituted by a halogen atom.

(3) Each of $R^5$ and $R^6$, which are independent of each other, is preferably a hydrogen atom, an alkyl group which may be substituted, $X^7CO-$ (wherein $X^7$ is as defined above), $X^8OCO-$ (wherein $X^8$ is an alkyl group which may be substituted, an alkenyl group which may be substituted, or an aryl group which may be substituted), a substituted carbamoyl group, an alkenyl group which may be substituted, an alkynyl group which may be substituted, a heteroaryl group which may be substituted, or $R^5$ and $R^6$ together form $=CR^7R^8$ (wherein each of $R^7$ and $R^8$, which are independent of each other, is a hydrogen atom, an alkyl group which may be substituted, a cycloalkyl group which may be substituted, an alkoxy group which may be substituted, an alkenyl group which may be substituted, or an amino group which may be substituted), more preferably a hydrogen atom, an alkyl group which may be substituted, $X^7CO-$ (wherein $X^7$ is a hydrogen atom, or an alkyl group which may be substituted), $X^8OCO-$ (wherein $X^8$ is an alkyl group which may be substituted), a substituted carbamoyl group, or $R^5$ and $R^6$ together form $=CR^7R^8$ (wherein each of $R^7$ and $R^8$, which are independent of each other, is a hydrogen atom, an alkyl group which may be substituted, a cycloalkyl group which may be substituted, an alkoxy group which may be substituted, or an amino group which may be substituted), most preferably $R^5$ is a hydrogen atom or an alkyl group, and $R^6$ is $X^7CO-$ (wherein $X^7$ is a hydrogen atom or an alkyl group), or $X^8OCO-$ (wherein $X^8$ is an alkyl group), or $R^5$ and $R^6$ together form $=CR^7R^8$ (wherein $R^7$ is a hydrogen atom, or an alkyl group, and $R^8$ is an amino group which may be substituted by an alkyl group, or an alkoxy group).

(4) The following compounds are most preferred among the compounds of the formulas (I) and (IX):
[4'-chloro-2-(4-trifluoromethylphenyl)acetophenone] N'-[1-(dimethylamino)ethylidene]hydrazone, [4'-fluoro-2-(4-trifluoromethylphenyl)acetophenone] N'-[1-(dimethylamino)ethylidene]hydrazone, ethyl 3-[1-(4-chlorophenyl)-2-(4-trifluoromethylphenyl)ethylidene]carbazate, [4'-chloro-2-(4-tert-butylphenyl)acetophenone] N'-[1-(dimethylamino)ethylidene]hydrazone, and [4'-fluoro-2-(4-tert-butylphenyl)acetophenone] N'-[1-(dimethyamino)ethylidene]hydrazone.

The compounds of the formulas (I) and (IX) may form salts with acidic substances or basic substances. Salts with acidic substances include inorganic acid salts such as hydrochlorides or sulfates. Salts with basic substances include salts with inorganic bases or organic bases, such as sodium salts, potassium salts, calcium salts, ammonium salts and dimethylamine salts.

Further, the compounds of the formulas (I) and (IX) have geometrical isomers, i.e. E-form and Z-form, by virtue of the double bond of the hydrazones. The present invention includes such isomers and mixtures of such isomers.

The compounds of the formula (I) can be prepared, for example, by the following Reaction Steps 1 to 7.

Reaction Step 1

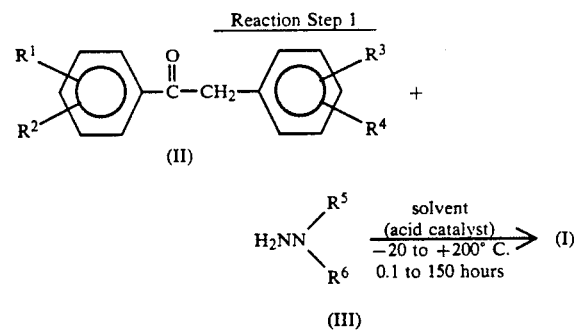

In the above formulas, $R^1$, $R^2$, $R^3$, $R^4$, $R^5$ and $R^6$ are as defined above.

A case where $R^5$ and $R^6$ together form $=CR^7R^8$.

Reaction Step 2

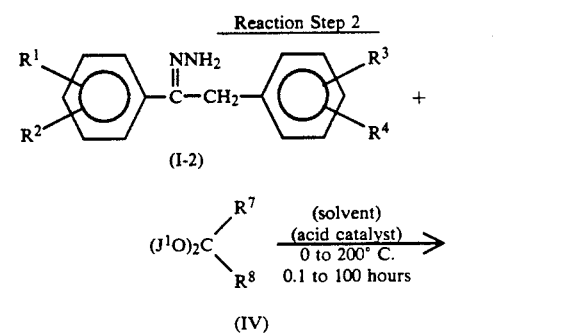

Reaction Step 2

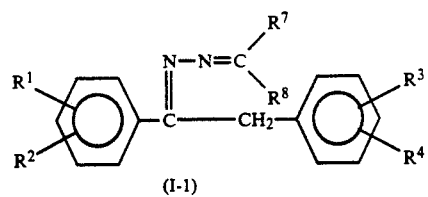

In the above formulas, $R^1$, $R^2$, $R^3$, $R^4$, $R^7$ and $R^8$ are as defined above, and $J^1$ is an alkyl group.

A case where $R^5$ and $R^6$ together form $=CR^7R^8$, wherein each of $R^7$ and $R^8$ is a hydrogen atom, an alkyl group which may be substituted, a cycloalkyl group which may be substituted, an alkenyl group which may be substituted, or an aryl group which may be substituted.

Reaction Step 3

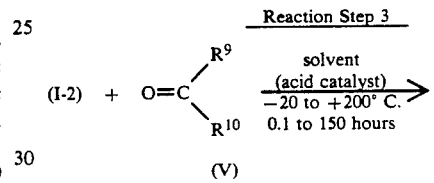

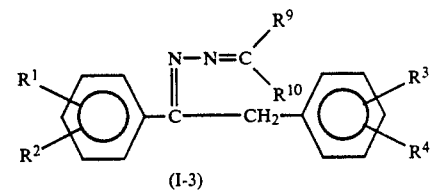

In the above formulas, $R^1$, $R^2$, $R^3$ and $R^4$ are as defined above, and each of $R^9$ and $R^{10}$, which are independent of each other, is a hydrogen atom, an alkyl group which may be substituted, a cycloalkyl group which may be substituted, an alkenyl group which may be substituted or an aryl group which may be substituted.

A case where $R^5$ and $R^6$ together from $=CR^7R^8$, wherein $R^8$ is an amino group which may be substituted, or a cyclic amino group which may be substituted.

Reaction Step 4

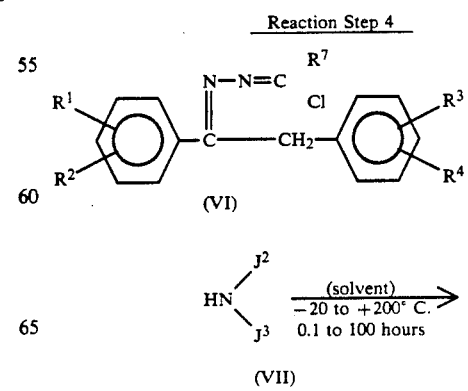

-continued
Reaction Step 4

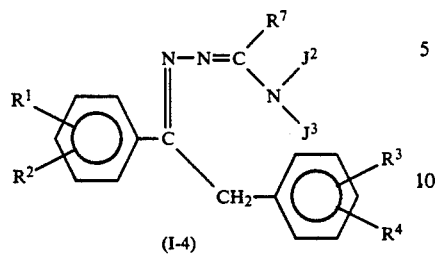

(I-4)

In the above formulas, $R^1$, $R^2$, $R^3$, $R^4$ and $R^7$ are as defined above, each of $J^2$ and $J^3$, which are independent of each other, is a hydrogen atom; an alkyl group which may be substituted by a halogen atom; an alkoxy group which may be substituted by a halogen atom; a phenyl group which may be substituted by a halogen atom or by an alkyl group which may be substituted by a halogen atom; a phenoxy group which may be substituted by a halogen atom or by an alkyl group which may be substituted by a halogen atom; a cyano group; an alkylamino group; an alkoxycarbonyl group, or $J^2$ and $J^3$ form together with the adjacent nitrogen atom, a cyclic amino group which may be substituted.

Reaction Step 5

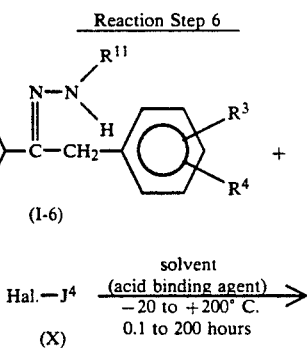

In the above formulas, $R^1$, $R^2$, $R^3$, $R^4$, $R^7$, $J^2$ and $J^3$ are as defined above A case where $R^6$ is $X^7CO-$, $X^8OCO-$, or $X^9SO_2-$.

Reaction Step 6

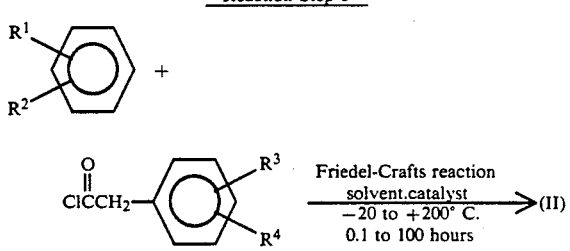

-continued
Reaction Step 6

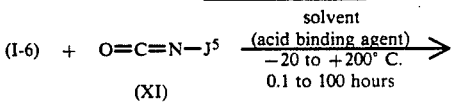

(I-5)

In the above formulas, $R^1$, $R^2$, $R^3$ and $R^4$ are as defined above, $R^{11}$ is a hydrogen atom, an alkyl group which may be substituted, $X^7CO-$, $X^8OCO-$, $X^9SO_2-$ (wherein $X^7$, $X^8$ and $X^9$ are as defined above), a carbamoyl group which may be substituted, an alkenyl group which may be substituted, an alkynyl group which may be substituted, or a heteroaryl group which may be substituted, and $J^4$, which is independent of $R^{11}$, is $X^7CO-$, $X^8OCO-$, $X^9SO_2-$ (wherein $X^7$, $X^8$ and $X^9$ are as defined above).

A case where $R^6$ is $J^5NHCO-$ (which is a part of a carbamoyl group which may be substituted).

Reaction Step 7

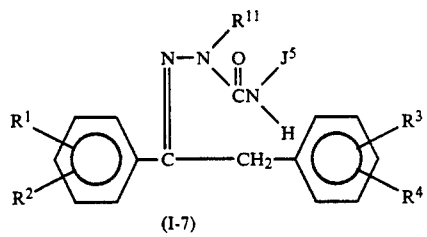

(I-7)

In the above formulas, $R^1$, $R^2$, $R^3$, $R^4$ and $R^{11}$ are as defined above, $J^5$ is an alkyl group which may be substituted by a halogen atom; a phenyl group which may be substituted by a halogen atom or by an alkyl group which may be substituted by a halogen atom; an alkylamino group; or an alkoxycarbonyl group.

In the Reaction Step 7, the hydrogen atom in $J^5NHCO-$ of the compound of the formula (I-7) can be alkylated by a usual alkylation reaction.

Further, the compounds of the formula (II) can be prepared, for example, by the following Reaction Steps 8 to 16.

Reaction Step 8

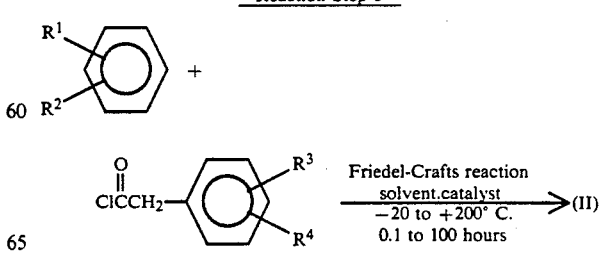

In the above formulas, $R^1$, $R^2$, $R^3$ and $R^4$ are as defined above.

Reaction Step 9

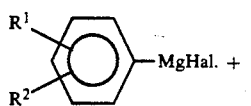

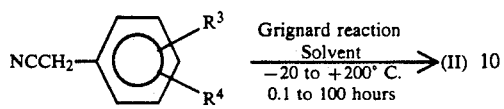

In the above formulas, $R^1$, $R^2$, $R^3$ and $R^4$ are as defined above, and Hal. is a halogen atom.

Reaction Step 10

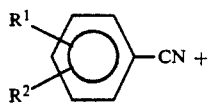

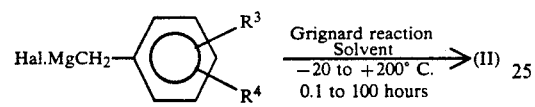

In the above formulas, $R^1$, $R^2$, $R^3$, $R^4$ and Hal. are as defined above.

Reaction Step 11

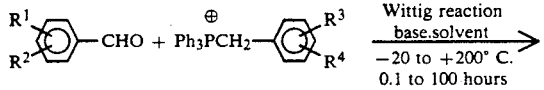

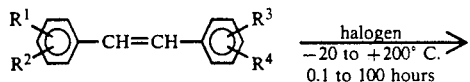

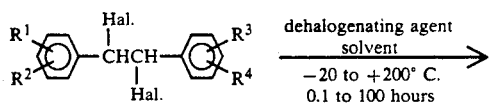

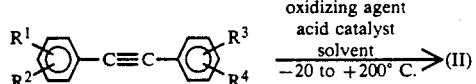

In the above formulas, $R^1$, $R^2$, $R^3$, $R^4$ and Hal. are as defined above, and Ph is a phenyl group.

Reaction Step 12

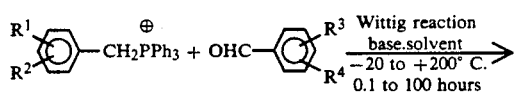

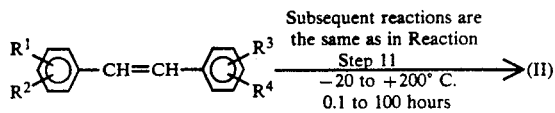

In the above formulas, $R^1$, $R^2$, $R^3$, $R^4$, Hal. and Ph are as defined above.

Reaction Step 13

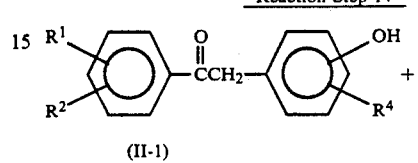

In the above formulas, $R^1$, $R^2$, $R^3$ and $R^4$ are as defined above.

A case where $R^3$ is $X^2CO_2$—, or $X^5SO_3$—.

Reaction Step 14

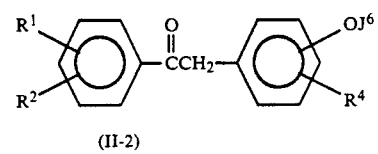

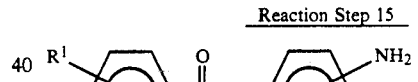

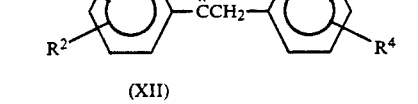

In the above formulas, $R^1$, $R^2$, $R^4$ and Hal. are as defined above, and $J^6$ is $X^2CO_2$—, or $X^5SO_2$— (wherein $X^2$ and $X^5$ are as defined above).

A case where $R^3$ is $X^1SO_2NH$—.

Reaction Step 15

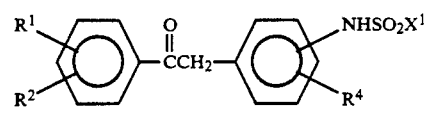

(XII)

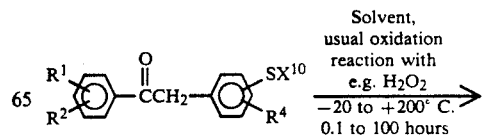

(II-3)

wherein $R^1$, $R^2$, $R^4$ and $X^1$ are as defined above.

A case where $R^3$ is $X^3SO$—, or $X^4SO_2$—.

Reaction Step 16

Solvent, usual oxidation reaction with e.g. $H_2O_2$
$-20$ to $+200°$ C.
0.1 to 100 hours (XIII)

-continued
Reaction Step 16

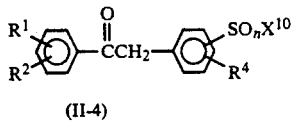

(II-4)

In the above formulas, $R^1$, $R^2$ and $R^4$ are as defined above, $X^{10}$ is the same as $X^3$ or $X^4$, and n is 1 or 2.

The compounds of the formula (I-2) can be prepared, for example, by the following Reaction Step 17.

Reaction Step 17

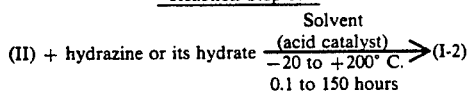

The compounds of the formula (VI) can be prepared, for example, by the following Reaction Step 18.

Reaction Step 18

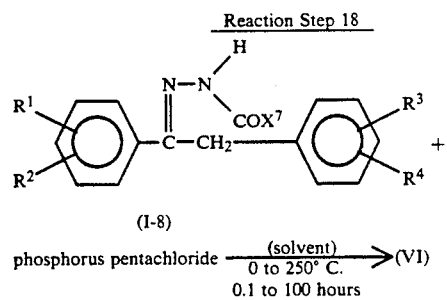

In the formula (I-8), $R^1$, $R^2$, $R^3$, $R^4$ and $R^7$ are as defined above.

The compounds of the formula (VIII) can be prepared, for example by the following Reaction Step 19.

Reaction Step 19

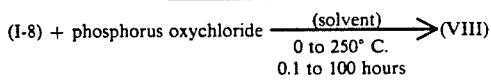

In the formula (I-8), $R^1$, $R^2$, $R^3$, $R^4$, $R^7$ and $X^7$ are as defined above.

The compounds of the formula (VI) can be prepared by the process for producing the compounds of the formula (I) or the compounds of the formula (I-2). The compounds of the formula (XII) and the compounds of the formula (XIII) can be prepared in the same manner as the process for producing the compounds of the formula (II). Further, the compounds of the formula (IX) which are outside the scope of the compounds of the formula (I), can also be prepared in accordance with the above processes.

The reactions of the above Reaction Steps 1, 3 and 17 are conducted usually in the presence of a solvent, and if necessary, in the presence of an acid catalyst, and the reaction temperatures are usually within a range of from $-20°$ to $+200°$ C., preferably from $-10°$ to $+150°$ C., and the reaction periods are usually from 0.1 to 150 hours. The solvent may, for example, be an ether such as diethyl ether, tetrahydrofuran or dioxane; an alcohol such as ethylene glycol, glycerol, methanol or ethanol; an aprotic polar solvent such as N,N-dimethylformamide, N,N-dimethylacetamide, N-methyl-2-pyrrolidone, dimethyl sulfoxide or sulforane; an aromatic hydrocarbon such as benzene, toluene or chlorobenzene; a halogenated hydrocarbon such as methylene chloride or chloroform; an aliphatic hydrocarbon such as pentane, hexane or heptane; an alicyclic hydrocarbon such as cyclohexane; a pyridine such as pyridine or picoline; acetic acid; or water. These solvents may be used in combination as a mixture. The acid catalyst may, for example, be a mineral acid such as hydrochloric acid, sulfuric acid or nitric acid; an organic acid such as formic acid, acetic acid, propionic acid, methane sulfonic acid, benzenesulfonic acid or p-toluenesulfonic acid; an acid addition salt of an amine such as pyridine hydrochloride or triethylamine hydrochloride. The reaction of the above Reaction Step 2 is conducted, if necessary, in the presence of a solvent and/or an acid catalyst, whereby the reaction temperature is usually from $0°$ to $200°$ C., preferably from $50°$ to $150°$ C., and the reaction time is usually from 0.1 to 100 hours. The solvent may, for example, be an ether, an alcohol, an aprotic polar solvent, an aromatic hydrocarbon, a halogenated hydrocarbon and water, as used in the above Reaction Steps 1, 3 and 17, as well as a nitrile such as acetonitrile. These solvents may be used in combination as a mixture. The acid catalyst may, for example, be the same as used in the above Reaction Steps 1, 3 and 17.

The reactions of the above Reaction Steps 4 and 5 are conducted, if necessary, in the presence of a solvent, whereby the reaction temperatures are usually from $-20°$ to $+200°$ C., preferably from $0°$ to $100°$ C., and the reaction periods are usually from 0.1 to 100 hours. The solvent may, for example, be an aromatic hydrocarbon, a pyridine, a halogenated hydrocarbon, an aliphatic hydrocarbon or water, as used in the above Reaction Steps 1, 3 and 17. These solvents may be used in combination as a mixture.

The reactions of the above Reaction Steps 6, 7, 14 and 15 are conducted usually in the presence of a solvent and if necessary in the presence of an acid binding agent, whereby the reaction temperatures are usually within a range of from $-20°$ to $+200°$ C., preferably from $0°$ to $150°$ C., and the reaction periods are usually from 0.1 to 100 hours. The solvent may, for example, be an inert organic solvent such as an ether, an aprotic polar solvent, an aromatic hydrocarbon, a halogenated hydrocarbon, an aliphatic hydrocarbon, an alicyclic hydrocarbon, a pyridine or water, as used in the above Reaction Steps 1, 3 and 17, or a nitrile such as acetonitrile. These solvents may be used in combination as a mixture. The acid binding agent may, for example, be a tertiary alkylamine such as triethylamine, an alkali metal carbonate such as sodium carbonate, or pyridine.

The reaction of the above Reaction Step 8 is a usual Friedel-Crafts reaction, which is conducted in the presence of a solvent and a catalyst. The reaction temperature is usually from $-20°$ to $+200°$ C., preferably from $-10°$ to $+100°$ C., and the reaction time is from 0.1 to 100 hours. The solvent may, for example, be carbon disulfide, a halogenated hydrocarbon as used in the above Reaction Step 1, 3 and 17, or nitrobenzene. The catalyst may, for example, be a Lewis acid such as aluminum chloride, lead chloride, ferrous chloride, ferric chloride, titanium tetrachloride, tin chloride, zinc chloride or polyphosphoric acid.

The reactions of the above Reaction Steps 9 and 10 are usual Grignard reactions, which are conducted in the presence of a solvent. The reaction temperatures are usually within a range of from $-20°$ to $+200°$ C., preferably from −10° to +100° C., and the reaction periods are from 0.1 to 100 hours. The solvent may be an ether as used in the above Reaction Steps 1, 3 and 17.

The first reaction in each of the above Reaction Steps 11 and 12 is a usual Wittig reaction, which is conducted in the presence of a base and a solvent. The reaction temperature is usually from −20° to +200° C. preferably from −10° to +150° C., and the reaction time is from 0.1 to 100 hours. The base may, for example, be a hydroxide, carbonate or acetate of an alkali metal or an alkaline earth metal, or an organo metallic compound such as butyllithium. The solvent may, for example, be an ether, an alcohol, an aprotic polar solvent, an aromatic hydrocarbon, a halogenated aromatic hydrocarbon, a halogenated hydrocarbon or water, as used in the above Reaction Steps 1, 3 and 17. These solvents may be used in combination as a mixture.

The second reaction in each of the above Reaction Steps 11 and 12 is a usual halogenation reaction, whereby a halogen (here, the halogen is preferably bromine or chlorine) is added in the presence of a peroxide or under irradiation with a light. The reaction temperature is usually form −20° to +200° C., preferably form −10° to +100° C., and the reaction time is from 0.1 to 100 hours. The solvent is preferably a hydrocarbon or a halogenated hydrocarbon, but other solvents as used in the above Reaction Step 1, 3 or 17 may also be employed.

The third reaction in each of the above Reaction Step 11 and 12 is a usual dehalogenation reaction, which is conducted by a dehalogenation agent in the presence of a solvent. The dehalogenation agent may, for example, be an alkali metal, or its alcoholate or hydroxide. The reaction temperature is usually from −20° to +200° C., preferably from −10° to +150° C., and the reaction time is from 0.1 to 100 hours. The solvent may be the same as used for the first reaction.

The fourth reaction in each of the above Reaction Steps 11 and 12 is a usual oxidation reaction, whereby oxidation is conducted by means of e.g. mercury (II) salt in the presence of an acid catalyst. The reaction temperature is usually from −20° to +200° C., preferably from −10° to +150° C., and the reaction time is from 0.1 to 100 hours. The solvent may be acetic acid or the same solvent as used for the first reaction. These solvents may be used in combination as a mixture. The acid catalyst may, for example, be an inorganic acid such as sulfuric acid or nitric acid, or an organic acid such as acetic acid or trifluoroacetic acid.

The reaction of the above Reaction Step 13 is a usual oxidation reaction, which is conducted in the presence of a solvent and an oxidizing agent. The reaction temperature is usually within a range of from −20° to +200° C., preferably form −10° to +150° C., and the reaction time is from 0.1 to 100 hours. The oxidizing agent may, for example, be a chromium (VI) salt, lead tetraacetate, nitric acid or dimethylsulfoxide. As the solvent, water or acetic acid is mainly used, but other solvents such as a hydrocarbon, a halogenated aromatic hydrocarbon, or an aprotic polar solvent, an aromatic hydrocarbon or a halogenated hydrocarbon, as used in the above Reaction Steps 1, 3 and 17, may also be used. These solvents may be used in combination as a mixture.

The reaction of the above Reaction Step 16 is a usual oxidation reaction with e.g. $H_2O_2$, which is conducted usually in the presence of a solvent. The reaction temperature is usually within the range of from −20° to +200° C., preferably from −10° to +100° C., and the reaction time is from 0.1 to 100 hours. The solvent may be the same solvent as used for the above Reaction Step 13. Such solvents may be used in combination as a mixture.

The reactions of the above Reaction Steps 18 and 19 are conducted, if necessary, in the presence of a solvent. The reaction temperature is usually from 0° to 250° C., preferably from 10° to 180° C., and the reaction time is from 0.1 to 100 hours. The solvent may, for example, be an aromatic hydrocarbon, a halogenated hydrocarbon, an aliphatic hydrocarbon, or an alicyclic hydrocarbon, as used in the above Reaction Steps 1, 3 and 17. These solvents may be used in combination as a mixture.

Now, specific Synthesis Examples of the compounds of the formula (I) will be described.

SYNTHESIS EXAMPLE 1

Synthesis of [4'-chloro-2-(4-chlorophenyl)acetophenone]N'-[1-dimethyamino)ethylidene]hydrazone (Compound No. 1)

(1) 1.33 g (5 mmol) of 4'-chloro-2-(4-chlorophenyl)acetophenone was dissolved in 25 ml of ethanol, and 1.25 g (25 mmol) of hydrazine monohydrate was added thereto. The mixture was refluxed under heating for 2 hours. After completion of the reaction, ethanol was distilled off under reduced pressure, and water was added to the residue. The mixture was extracted with dichloromethane. The extract was dried over anhydrous sodium sulfate. Then, the solvent was distilled off to obtain 1.44 g of [4'-chloro-2-(4-chlorophenyl)acetophenone]hydrazone as a yellow oily substance.

(2) To 1.0 g (3.6 mmol) of [4'-chloro-2-(4-chlorophenyl)acetophenone]hydrazone obtained in the above step (1), 0.51 g (4.2 mmol) of N,N-dimethylacetamidedimethylacetal was added, and the mixture was heated at 120° C. for 2 hours. After completion of the reaction, the reaction solution was purified by silica gel column chromatography (developing solvent:ethyl acetate/n-hexane = ¼) to obtain 0.56 g of the desired product (Compound No. 1) having a melting point of from 125° to 127° C.

SYNTHESIS EXAMPLE 2

Synthesis of methyl 3-[1,2-bis(4-chlorophenyll)ethylidene]carbazate (Compound No. 201)

0.43 g (1.5 mmol) of [4'-chloro-2-(4-chlorophenyl)acetophenone]hydrazone obtained in Synthesis Example 1 (1), was dissolved in 5 ml of pyridine, and 0.2 ml (2.5 mmol) of methyl chlorocarbonate was dropwise added thereto under cooling with ice. After completion of the dropwise addition, the mixture was stirred at room temperature for 3 hours. After completion of the reaction, the mixture was put into water and extracted with dichloromethane. The extract was dried over anhydrous sodium sulfate and then concentrated under reduced pressure. The residue was purified by silica gel column chromatography (developing solvent: ethyl acetate/n-hexane = 3/7) to obtain 0.37 g of the desired product (Compound No. 201) having a melting point of from 156° to 159° C.

SYNTHESIS EXAMPLE 3

Synthesis of
[4'-chloro-2-(4-chlorophenyl)acetophenone]-4-(4-trifluoromethylphenyl)semicarbazone (Compound No. 200)

0.97 g (6 mmol) of p-aminobenzotrifluoride was dissolved in 10 ml of ethyl acetate, and 1.1 ml (9 mmol) of trichloromethyl chloroformate was added thereto. The mixture was refluxed under heating for 2 hours. Then, excess trichloromethyl chloroformate and ethyl acetate were distilled off under reduced pressure.

The residue was dissolved in 5 ml of ethyl ether, and the solution was dropwise added under cooling with ice to 20 ml of a diethyl ether solution containing 1.4 g (5 mmol) of [4'-chloro-2-(4-chlorophenyl)acetophenone]-hydrazone obtained in the same manner as Synthesis Example 1 (1). After completion of the dropwise addition, the mixture was stirred at room temperature for 1.5 hours.

After completion of the reaction, the solvent was distilled off, and a small amount of water was added to the residue. The mixture was extracted with dichloromethane, and the extract was dried over anhydrous sodium sulfate and then concentrated under reduced pressure. The residue was purified by silica gel column chromatography (developing solvent: ethyl acetate/n-hexane=¼) to obtain 1.53 g of the desired compound (Compound No. 200) having a melting point of from 194° to 198° C.

SYNTHESIS EXAMPLE 4

Synthesis of [4'-chloro-2-(4-tert-butyl)acetophenone] N'-[1-(dimethylamino)ethylidene]hydrazone (Compound No. 32)

(1) 0.7 of magnesium(scraped shape) and 100 mg of a chip of iodine were added to 5 ml of anhydrous diethyl ether. 10 ml of anhydrous diethyl ether solution of 5.6 g of p-bromochlorobenzene was dropwise added thereto under nitrogen stream at a rate that was just fast enough to maintain a gentle reflux. This solution was stirred at room temperature for 20 minutes to react them, a solution of 4.8 g of p-tert-butylphenyl acetonitrile in 5 ml of anhydrous diethyl ether was dropwise added thereto at a rate that was just fast enough to maintain a gentle reflux. The solution was further stirred for 30 minutes to react them. After completion of the reaction, a mixture solution of 10 g of ice and 130 ml of 6N-hydrochloric acid was added thereto and a reaction product was extracted with ethyl acetate. The extract was washed with water and a saturated aqueous solution of sodium chloride, dried over anhydrous sodium sulfate, and concentrated under reduced pressure. The redisue was purified by silica gel column chromatography (developing solvent: ethyl acetate/n-hexane=1/9) to obtain 1.3 g of 4'-chloro-2-(4-tert-butylphenyl)acetophenone. (2) 1.3 g of (4.5 mmol) of 4'-chloro-2-(4-tert-butylphenyl)acetophenone was dissolved in 15 ml of ethanol, and 0.2 g (4.5 mmol) of hydrazine monohydrate was added thereto. The mixture was refluxed under heating for three hours. After completion of the reaction, ethanol was distilled off under reduced pressure. Water was added to the residue, and the mixture was extracted with dichloromethane. The extract was dried over anhydrous sodium sulfate, and the solvent was distilled off to obtain 1.3 g of [4'-chloro-2-(4-tert-butylphenyl)acetophenone]hydrazone as a yellow oily substance.

(3) 1.3 g (4.3 mmol) of [4'-chloro-2-(4-tert-butylphenyl)acetophenone]hydrazone obtained in the above step (2) was dissolved in 15 ml of acetonitrile, and 0.6 g (4.7 mmol) of N'N-dimethylacetoamidedimethylacetal was added thereto. The mixture was refluxed under heating for 24 hours. After completion of the reaction, acetonitrile was distilled off under reduced pressure, and the residue was purified by silica gel column chromatography (developing solvent: ethyl acetate/n-hexane=1/8) to obtain 0.4 g of the desired compound (Compound No. 32) having a melting point of from 100° to 101° C.

SYNTHESIS EXAMPLE 5

Synthesis of [4'-fluoro-2-4-trifluoromethylphenyl)acetophenone]N'-[1-(dimethyamino]ethylidene]hydrazone ( Compound No. 38)

(1) 8.9 g of (72 mmol) of 4-fluorobenzaldehyde and 32 g (72 mmol) of (4-trifluromethylbenzyl)triphenylphosphonium chloride were dissolved in 300 ml of methylene chloride. While vigorously stirring the solution, 280 ml (0.84 mol) of 3N sodium hydroxide was dropwise added at room temperature. After completion of the dropwise addition, the mixture was stirred at room temperature for 2 hours. After completion of the reaction, the mixture was subjected to liquid separation. The organic layer was washed twice with water and then dried over anhydrous sodium sulfate. Then, the solvent was distilled off. The residue was purified by silica gel column chromatography (developing solvent: n-hexane) to obtain 12.4 g of 4-fluoro-4'-trifluoromethylstilbene.

(2) 12.4 g (47 mmol) of 4-fluoro-4'-trifluoromethylstilbene was dissolved in 80 ml of chloroform. While irradiating the solution with a light of 160W mercury lamp, a solution of 2.4 ml (47 mmol) of bromine in 20 ml of chloroform was dropwise added at 40° C. Then, stirring was continued for 30 minutes. After completion of the reaction, the solvent was distilled off to obtain a yellow oily substance. Without purification, this oily substance was dissolved in 100 ml of ethanol. While refluxing the solution under heating, a solution of 12.3 g of potassium hydroxide in 45 ml of water was dropwise added. After completion of the dropwise addition, refluxing under heating was continued for 3 hours. After completion of the reaction, ethanol was distilled off, and water was added to the residue. The mixture was extracted with diethyl ether and then dried over anhydrous sodium sulfate. Then, the solvent was distilled off to obtain 12.2 g of 4-fluoro-4'-trifluoromethyltolane as a yellow solid. Without purification, this yellow solid was used for the subsequent reaction.

(3) To 12.2 g (46 mmol) of 4-fluoro-4'-trifluoromethyltolane, 60 ml of water, 60 ml of acetic acid, 40 ml of sulfuric acid and 13.6 g (46 mmol) of mercuric sulfate were added, and the mixture was stirred at 90° C. for 3.5 hours. After completion of the reaction, water was added to the reaction mixture, and the mixture was extracted with diethyl ether. The extract was dried over anhydrous sodium sulfate, and the solvent was distilled off. The residue was purified by silica gel column chromatography (developing solvent: ethyl acetate/n-hexane=1/9) to obtain 5.1 g of 4'-fluoro-2- (4-trifluoromethylphenyl)acetophenone having a melting point of from 87° to 89° C.

(4) 5.1 g (18.1 mmol) of 4'-fluoro-2-(4-trifluoromethylphenyl)acetophenone was dissolved in 100 ml of ethanol, and 8.8 ml (181 mmol) of hydrazine monohydrate was added thereto. The mixture was refluxed under heating for 2 hours. After completion of the reaction, ethanol was distilled off under reduced pressure, and water was added to the residue. The mixture was extracted with dichloromethane. The extract was dried over an hydrous sodium sulfate, and the solvent was distilled off to obtain [4'-fluoro-2-(4-trifluoromethylphenyl)acetophenone]hydrazone as a yellow oily substance.

(5) To [4'-fluoro-2-(4-trifluoromethylphenyl)acetophenone]hydrazone obtained in the above step (4), 3.13 g (23.5 mmol) of N'N-dimethylacetamidedimethylacetal was added. The mixture was heated at 120° C. for 2 hours. After completion of the reaction, the residue was purified by silica gel column chromatography (developing solvent: ethyl acetate/n-hexane=1/19) to obtain 3.10 g of the desired product (Compound No. 38) having a melting point of from 86° to 88° C.

SYNTHESIS EXAMPLE 6

Synthesis of [4'-chloro-2-(4-trifluoromethylphenyl)acetophenone]N'-[1-(dimethylamino)ethylidene]hydrazone (Compound No. 9)

The synthesis was conducted in substantially the same manner as in Synthesis Example 5 except that 4-fluorobenzaldehyde in Synthesis Example 5 (1) was changed to 4-chlorobenzaldehyde to obtain the desired product (Compound No. 9) having a melting point of from 94° to 97° C.

SYNTHESIS EXAMPLE 7

Synthesis of [4'-fluoro-2-(4-tert-buthylphenyl)acetophenone]N'-[1-(dimethylamino)ethylidene]hydrazone (Compound No. 60)

(1) A mixture of 3 g (11 mmol) of 4'-fluoro-2-(4-tert-butylphenyl)acetophenone, 0.8 g (11 mmol) of acetyl hydrazide, 60 mg of acetic acid and 20 ml of ethanol was refluxed under heating for 20 hours. After completion of the reaction, ethanol was distilled off under reduced pressure to concentrate a reaction product. It was purified by silica gel column chromatography (developing solvent: n hexane/ethyl acetate=4/1) to obtain 1.09 g of [4'-fluoro-2-(4-tert-butylphenyl)acetophenone] N'-(acetyl)hydrazone having a melting point of 132° to 134° C. (2) A mixture solution of 1 g of [4'-fluoro-2-(4-tert-butylphenyl)acetophenone] N'-(acetyl)hydrazone, 0.64 g of phosphorus pentachloride and 15 ml of dichloromethane was stirred at room temperature for one hour and refluxed under heating for 2 hours to react them. After completion of the reaction, a reaction solution was concentrated under reduced pressure, 10 ml of dichloromethane was added and 1.38 g of dimethylamine was further added one time thereto at room temperature to react them at the same temperature for 2 hours with stirring. After completion of the reaction, a reaction product was diluted with 30 ml of dichloromethane, washed with water, and dried over anhydrous sodium sulfate. The solvent was distilled off under reduced pressure to concentrate it. It was purified by silica gel column chromatography (developing solvent: n-hexane/ethyl acetate=9/1) to obtain 0.33 g of the desired product (Compound No. 60) having a melting point of 65° to 67° C.

Now, typical examples of the compound of the formula (I) will be given in the following Tables 1 and 2.

TABLE 1

(I-1)

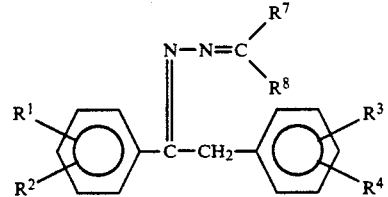

| Compound No. | $R^1$ | $R^2$ | $R^3$ | $R^4$ | $R^7$ | $R^8$ | Physical properties |
|---|---|---|---|---|---|---|---|
| 1 | 4-Cl | H | 4-Cl | H | $CH_3$ | $-N(CH_3)_2$ | m.p. 125–127° C. |
| 2 | 4-Cl | H | 4-F | H | $CH_3$ | $-N(CH_3)_2$ | m.p. 114–119° C. |
| 3 | 4-Cl | H | 4-$OCH_3$ | H | $CH_3$ | $-N(CH_3)_2$ | m.p. 93–105° C. |
| 4 | 4-Cl | H | 3-Cl | 4-Cl | $CH_3$ | $-N(CH_3)_2$ | m.p. 92–96° C. |
| 5 | 4-Cl | H | 2-Cl | H | $CH_3$ | $-N(CH_3)_2$ | m.p. 118–122° C. |
| 6 | 4-Cl | H | 3-Cl | H | $CH_3$ | $-N(CH_3)_2$ | m.p. 64–68° C. |
| 7 | 4-F | H | 4-Cl | H | $CH_3$ | $-N(CH_3)_2$ | m.p. 101–106° C. |
| 8 | 4-Cl | H | 4-$CH_3$ | H | $CH_3$ | $-N(CH_3)_2$ | m.p. 115–119° C. |
| 9 | 4-Cl | H | 4-$CF_3$ | H | $CH_3$ | $-N(CH_3)_2$ | m.p. 94–97° C. |
| 10 | 4-Cl | H | 4-$OSO_2CF_3$ | H | $CH_3$ | $-(N(CH_3)_2$ | $n_D^{16.9}$1.5858 |
| 11 | 4-Cl | H | 4-$OSO_2CH_3$ | H | $CH_3$ | $-N(CH_3)_2$ | m.p. 112–117° C. |

TABLE 1-continued (I-1)

$$\underset{R^2}{\overset{R^1}{\bigcirc}}\!\!-\!\!\underset{CH_2}{\overset{N-N=C}{C}}\!\!\underset{R^8}{\overset{R^7}{\bigcirc}}\!\!\underset{R^4}{\overset{R^3}{\bigcirc}}$$

| Compound No. | $R^1$ | $R^2$ | $R^3$ | $R^4$ | $R^7$ | $R^8$ | Physical properties |
|---|---|---|---|---|---|---|---|
| 12 | 4-F | H | 4-F | H | $CH_3$ | $-N(CH_3)_2$ | m.p. 78–84° C. |
| 13 | 4-F | H | 3-Cl | 4-Cl | $CH_3$ | $-N(CH_3)_2$ | |
| 14 | 4-F | H | 3-F | 4-Cl | $CH_3$ | $-N(CH_3)_2$ | |
| 15 | 4-$CF_3$ | H | 4-Cl | H | $CH_3$ | $-N(CH_3)_2$ | m.p. 100–101° C. |
| 16 | 4-Cl | H | 3-Cl | 4-$CF_3$ | $CH_3$ | $-N(CH_3)_2$ | |
| 17 | 4-Cl | H | 4-Br | H | $CH_3$ | $-N(CH_3)_2$ | m.p. 131–132° C. |
| 18 | 4-Cl | H | 4-$OCF_3$ | H | $CH_3$ | $-N(CH_3)_2$ | |
| 19 | 4-Cl | H | 4-$SCF_3$ | H | $CH_3$ | $-N(CH_3)_2$ | |
| 20 | 4-$CF_3$ | H | 4-$CF_3$ | H | $CH_3$ | $-N(CH_3)_2$ | m.p. 114–116° C. |
| 21 | 4-Cl | H | 2-Cl | 4-$CF_3$ | $CH_3$ | $-N(CH_3)_2$ | |
| 22 | 4-$SCH_3$ | H | 4-$SO_2CH_3$ | H | Ph | $-OCH_3$ | |
| 23 | 4-COOH | 3-CN | 3-Cl | H | $CH=CH_2$ | $-N(CH_3)_2$ | |
| 24 | 4-Cl | H | 4-$SCH_3$ | H | $CH_3$ | $-N(CH_3)_2$ | |
| 25 | 4-Cl | H | 4-OH | H | $CH_3$ | $-N(CH_3)_2$ | m.p. 167–171° C. |
| 26 | 4-Cl | H | 4-COOH | H | $CH_3$ | $-N(CH_3)_2$ | |
| 27 | 4-Cl | H | 4-$NHSO_2CH_3$ | H | $CH_3$ | $-N(CH_3)_2$ | |
| 28 | 4-Cl | H | 4-$OCOCH_3$ | H | $CH_3$ | $-N(CH_3)_2$ | |
| 29 | 4-Cl | H | 4-$OPO(OCH_3)_2$ | H | $CH_3$ | $-N(CH_3)_2$ | |
| 30 | 4-Cl | H | 3-$CF_3$ | H | $CH_3$ | $-N(CH_3)_2$ | m.p. 95–97° C. |
| 31 | 4-Cl | H | 2-Cl | 6-Cl | $CH_3$ | $-N(CH_3)_2$ | m.p. 113–120° C. |
| 32 | 4-Cl | H | 4-t-Bu | H | $CH_3$ | $-N(CH_3)_2$ | m.p. 100–101° C. |
| 33 | 4-Cl | H | 4-$Si(CH_3)_3$ | H | $CH_3$ | $-N(CH_3)_2$ | $n_D^{27.0}$1.6172 |
| 34 | H | H | 4-$CF_3$ | H | $CH_3$ | $-N(CH_3)_2$ | m.p. 95–98° C. |
| 35 | 4-Cl | H | 4-O–⌬(Cl, $CF_3$) | H | $CH_3$ | $-N(CH_3)_2$ | $n_D^{27.8}$1.600 |
| 36 | 4-Cl | H | 4-$OSO_2$–⌬($CF_3$) | H | $CH_3$ | $-N(CH_3)_2$ | $n_D^{26.4}$1.6104 |
| 37 | 4-Cl | H | 4-$OCHF_2$ | H | $CH_3$ | $-N(CH_3)_2$ | m.p. 72° C. |
| 38 | 4-F | H | 4-$CF_3$ | H | $CH_3$ | $-N(CH_3)_2$ | m.p. 86–88° C. |
| 39 | 4-Cl | H | 4-iso-Pr | H | $CH_3$ | $-N(CH_3)_2$ | m.p. 92–94° C. |
| 40 | 4-Cl | H | 4-$OCOOC_2H_5$ | H | $CH_3$ | $-N(CH_3)_2$ | m.p. 75–76° C. |
| 41 | 4-$C_2H_5$ | H | 4-$CF_3$ | H | $CH_3$ | $-N(CH_3)_2$ | m.p. 78–80° C. |
| 42 | 4-$CH_3$ | H | 4-$CF_3$ | H | $CH_3$ | $-N(CH_3)_2$ | m.p. 99–100° C. |
| 43 | 3-Cl | 4-Cl | 4-$CF_3$ | H | $CH_3$ | $-N(CH_3)_2$ | m.p. 79–81° C. |
| 44 | 4-Br | H | 4-$CF_3$ | H | $CH_3$ | $-N(CH_3)_2$ | m.p. 130–131° C. |
| 45 | 4-t-Bu | H | 4-t-Bu | H | $CH_3$ | $-N(CH_3)_2$ | $n_D^{38.8}$1.5808 |
| 46 | 2-Cl | H | 4-Cl | H | $CH_3$ | $-N(CH_3)_2$ | $n_D^{21.8}$1.6292 |
| 47 | 4-$CF_3$ | H | 4-t-Bu | H | $CH_3$ | $-N(CH_3)_2$ | m.p. 106–108° C. |
| 48 | 2-F | H | 4-Cl | H | $CH_3$ | $-N(CH_3)_2$ | $n_D^{22.0}$1.6194 |
| 49 | 4-F | H | 4-Br | H | $CH_3$ | $-N(CH_3)_2$ | m.p. 109–110° C. |
| 50 | 4-Ph | H | 4-Cl | H | $CH_3$ | $-N(CH_3)_2$ | m.p. |

TABLE 1-continued (I-1)

$$\text{structure with } R^1, R^2, R^3, R^4, R^7, R^8 \text{ substituents on the diarylmethane-hydrazone backbone}$$

| Compound No. | R¹ | R² | R³ | R⁴ | R⁷ | R⁸ | Physical properties |
|---|---|---|---|---|---|---|---|
| | | | | | | | 139–143° C. |
| 51 | 4-Cl-C₆H₄- | H | 4-Cl | H | CH₃ | —N(CH₃)₂ | m.p. 140–143° C. |
| 52 | 4-CF₃ | H | 4-F | H | CH₃ | —N(CH₃)₂ | m.p. 112–115° C. |
| 53 | 4-t-Bu | H | 4-F | H | CH₃ | —N(CH₃)₂ | m.p. 110–112° C. |
| 54 | 4-CF₃ | H | 4-CH₃ | H | CH₃ | —N(CH₃)₂ | m.p. 105–106° C. |
| 55 | 4-CH₃ | H | 4-Br | H | CH₃ | —N(CH₃)₂ | m.p. 123–125° C. |
| 56 | 4-Br | H | 4-Br | H | CH₃ | —N(CH₃)₂ | m.p. 150° C. |
| 57 | 3-F | 4-F | 4-t-Bu | H | CH₃ | —N(CH₃)₂ | $n_D^{16.0}$1.5994 |
| 58 | 3-F | 4-F | 4-Br | H | CH₃ | —N(CH₃)₂ | m.p. 115–116° C. |
| 59 | 4-F | H | 3-F | 4-F | CH₃ | —N(CH₃)₂ | m.p. 84° C. |
| 60 | 4-F | H | 4-t-Bu | H | CH₃ | —N(CH₃)₂ | m.p. 65–67° C. |
| 61 | 4-Cl | H | 4-Cl | H | H | —N(CH₃)₂ | m.p. 97–98° C. |
| 62 | 4-Cl | H | 4-Cl | H | CH₃ | —OCH₃ | $n_D^{38.8}$1.6042 |
| 63 | 4-Ph | H | 4-Cl | H | CH₃ | —OCH₃ | m.p. 92–96° C. |
| 64 | 4-CF₃ | H | 4-t-Bu | H | CH₃ | —OCH₃ | $n_D^{20.8}$1.5406 |
| 65 | 4-CF₃ | H | 4-CF₃ | H | CH₃ | —OC₂H₅ | $n_D^{21.2}$1.5094 |
| 66 | 4-CH₃ | H | 4-Br | H | CH₃ | —OC₂H₅ | $n_D^{18.2}$1.5890 |
| 67 | 4-Cl | H | 4-CF₃ | H | CH₃ | NH₂ | |
| 68 | 4-Cl | H | 4-t-Bu | H | CH₃ | NH₂ | |
| 69 | 4-F | H | 4-CF₃ | H | CH₃ | NH₂ | |
| 70 | 4-F | H | 4-t-Bu | H | CH₃ | NH₂ | |
| 71 | 4-Cl | H | 4-CO₂CH₃ | H | CH₃ | —N(CH₃)₂ | |
| 72 | 4-Cl | H | 4-COCH₃ | H | CH₃ | —N(CH₃)₂ | |
| 73 | 4-Cl | H | 4-OCHCH₃ \| CF₃ | H | CH₃ | —N(CH₃)₂ | |
| 74 | 4-F | H | 4-(1,1-dimethylpropyl) | H | CH₃ | —N(CH₃)₂ | $n_D^{16.2}$1.6037 |
| 75 | 4-Cl | H | 4-Cl | H | CH₃ | iso-Pr | $n_D^{23.0}$1.6006 |
| 76 | 4-Cl | H | 4-Cl-C₆H₄- | H | CH₃ | —N(CH₃)₂ | m.p. 113–117° C. |
| 77 | 4-F | H | 4-t-Bu | H | CH₃ | —NHCH₃ | |
| 78 | 4-F | H | 4-CF₃ | H | CH₃ | —NHCH₃ | |
| 79 | 4-Cl | H | 4-t-Bu | H | CH₃ | —NHCH₃ | |
| 80 | 4-Cl | H | 4-CF₃ | H | CH₃ | —NHCH₃ | |
| 81 | 4-CH₃ | H | 4-t-Bu | H | CH₃ | —NHCH₃ | |
| 82 | 4-CH₃ | H | 4-CF₃ | H | CH₃ | —NHCH₃ | |
| 83 | 4-CH₃ | H | 4-t-Bu | H | CH₃ | —NH₂ | |
| 84 | 4-CH₃ | H | 4-CF₃ | H | CH₃ | —NH₂ | |
| 85 | 4-F | H | 4-t-Bu | H | CH₃ | —NHC₂H₅ | |
| 86 | 4-F | H | 4-CF₃ | H | CH₃ | —NHC₂H₅ | |
| 87 | 4-Cl | H | 4-t-Bu | H | CH₃ | —NHC₂H₅ | |
| 88 | 4-Cl | H | 4-CF₃ | H | CH₃ | —NHC₂H₅ | |
| 89 | 4-CH₃ | H | 4-t-Bu | H | CH₃ | —NHC₂H₅ | |
| 90 | 4-CH₃ | H | 4-CF₃ | H | CH₃ | —NHC₂H₅ | |

TABLE 1-continued

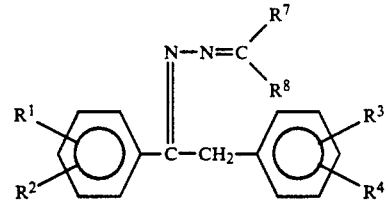

(I-1)

| Compound No. | $R^1$ | $R^2$ | $R^3$ | $R^4$ | $R^7$ | $R^8$ | Physical properties |
|---|---|---|---|---|---|---|---|
| 91 | 4-F | H | 4-t-Bu | H | $CH_3$ | $-N(CH_3)(C_2H_5)$ | |
| 92 | 4-F | H | 4-$CF_3$ | H | $CH_3$ | $-N(CH_3)(C_2H_5)$ | |
| 93 | 4-Cl | H | 4-t-Bu | H | $CH_3$ | $-N(CH_3)(C_2H_5)$ | |
| 94 | 4-Cl | H | 4-$CF_3$ | H | $CH_3$ | $-N(CH_3)(C_2H_5)$ | |
| 95 | 4-$CH_3$ | H | 4-t-Bu | H | $CH_3$ | $-N(CH_3)(C_2H_5)$ | |
| 96 | 4-$CH_3$ | H | 4-$CF_3$ | H | $CH_3$ | $-N(CH_3)(C_2H_5)$ | |
| 97 | 4-F | H | 4-t-Bu | H | $CH_3$ | $-N(C_2H_5)_2$ | |
| 98 | 4-F | H | 4-$CF_3$ | H | $CH_3$ | $-N(C_2H_5)_2$ | |
| 99 | 4-Cl | H | 4-t-Bu | H | $CH_3$ | $-N(C_2H_5)_2$ | |
| 100 | 4-Cl | H | 4-$CF_3$ | H | $CH_3$ | $-N(C_2H_5)_2$ | |
| 101 | 4-$CH_3$ | H | 4-t-Bu | H | $CH_3$ | $-N(C_2H_5)_2$ | |
| 102 | 4-$CH_3$ | H | 4-$CF_3$ | H | $CH_3$ | $-N(C_2H_5)_2$ | |
| 103 | 4-F | H | 4-t-Bu | 3-F | $CH_3$ | $-N(CH_3)_2$ | |
| 104 | 4-F | H | 4-$CF_3$ | 3-F | $CH_3$ | $-N(CH_3)_2$ | |
| 105 | 4-Cl | H | 4-t-Bu | 3-F | $CH_3$ | $-N(CH_3)_2$ | |
| 106 | 4-Cl | H | 4-$CF_3$ | 3-F | $CH_3$ | $-N(CH_3)_2$ | |
| 107 | 4-$CH_3$ | H | 4-t-Bu | 3-F | $CH_3$ | $-N(CH_3)_2$ | |
| 108 | 4-$CH_3$ | H | 4-$CF_3$ | 3-F | $CH_3$ | $-N(CH_3)_2$ | |
| 109 | 4-F | H | 3-t-Bu | H | $CH_3$ | $-N(CH_3)_2$ | |
| 110 | 4-F | H | 3-$CF_3$ | H | $CH_3$ | $-N(CH_3)_2$ | |
| 111 | 4-Cl | H | 3-t-Bu | H | $CH_3$ | $-N(CH_3)_2$ | |
| 112 | 4-$CH_3$ | H | 3-t-Bu | H | $CH_3$ | $-N(CH_3)_2$ | |
| 113 | 4-$CH_3$ | H | 3-$CF_3$ | H | $CH_3$ | $-N(CH_3)_2$ | |
| 114 | 4-F | H | 4-t-Bu | 3-Cl | $CH_3$ | $-N(CH_3)_2$ | |
| 115 | 4-F | H | 4-$CF_3$ | 3-Cl | $CH_3$ | $-N(CH_3)_2$ | |
| 116 | 4-Cl | H | 4-t-Bu | 3-Cl | $CH_3$ | $-N(CH_3)_2$ | |
| 117 | 4-$CH_3$ | H | 4-t-Bu | 3-Cl | $CH_3$ | $-N(CH_3)_2$ | |
| 118 | 4-$CH_3$ | H | 4-$CF_3$ | 3-Cl | $CH_3$ | $-N(CH_3)_2$ | |
| 119 | 4-F | H | 4-t-Bu | H | $CH_3$ | $OCH_3$ | |
| 120 | 4-F | H | 4-$CF_3$ | H | $CH_3$ | $OCH_3$ | |
| 121 | 4-Cl | H | 4-t-Bu | H | $CH_3$ | $OCH_3$ | |
| 122 | 4-Cl | H | 4-$CF_3$ | H | $CH_3$ | $OCH_3$ | |
| 123 | 4-$CH_3$ | H | 4-t-Bu | H | $CH_3$ | $OCH_3$ | |
| 124 | 4-$CH_3$ | H | 4-$CF_3$ | H | $CH_3$ | $OCH_3$ | |
| 125 | 4-F | 3-F | 4-$CF_3$ | H | $CH_3$ | $-N(CH_3)_2$ | |
| 126 | 4-Cl | 3-F | 4-t-Bu | H | $CH_3$ | $-N(CH_3)_2$ | |
| 127 | 4-Cl | 3-F | 4-$CF_3$ | H | $CH_3$ | $-N(CH_3)_2$ | |
| 128 | 4-$CH_3$ | 3-F | 4-t-Bu | H | $CH_3$ | $-N(CH_3)_2$ | |
| 129 | 4-$CH_3$ | 3-F | 4-$CF_3$ | H | $CH_3$ | $-N(CH_3)_2$ | |
| 130 | 4-F | 3-Cl | 4-t-Bu | H | $CH_3$ | $-N(CH_3)_2$ | |
| 131 | 4-F | 3-Cl | 4-$CF_3$ | H | $CH_3$ | $-N(CH_3)_2$ | |
| 132 | 4-Cl | 3-Cl | 4-t-Bu | H | $CH_3$ | $-N(CH_3)_2$ | |
| 133 | 4-$CH_3$ | 3-Cl | 4-t-Bu | H | $CH_3$ | $-N(CH_3)_2$ | |
| 134 | 4-$CH_3$ | 3-Cl | 4-$CF_3$ | H | $CH_3$ | $-N(CH_3)_2$ | |
| 135 | 4-F | H | 4-t-Bu | H | H | $-N(CH_3)_2$ | |
| 136 | 4-F | H | 4-$CF_3$ | H | H | $-N(CH_3)_2$ | |
| 137 | 4-Cl | H | 4-t-Bu | H | H | $-N(CH_3)_2$ | |
| 138 | 4-Cl | H | 4-$CF_3$ | H | H | $-N(CH_3)_2$ | |
| 139 | 4-$CH_3$ | H | 4-t-Bu | H | H | $-N(CH_3)_2$ | |
| 140 | 4-$CH_3$ | H | 4-$CF_3$ | H | H | $-N(CH_3)_2$ | |

TABLE 1-continued

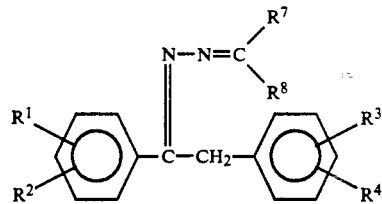
(I-1)

| Compound No. | R¹ | R² | R³ | R⁴ | R⁷ | R⁸ | Physical properties |
|---|---|---|---|---|---|---|---|
| 141 | 4-F | H | 4-t-Bu | H | $C_2H_5$ | $-N(CH_3)_2$ | |
| 142 | 4-F | H | 4-$CF_3$ | H | $C_2H_5$ | $-N(CH_3)_2$ | |
| 143 | 4-Cl | H | 4-t-Bu | H | $C_2H_5$ | $-N(CH_3)_2$ | |
| 144 | 4-Cl | H | 4-$CF_3$ | H | $C_2H_5$ | $-N(CH_3)_2$ | |
| 145 | 4-$CH_3$ | H | 4-t-Bu | H | $C_2H_5$ | $-N(CH_3)_2$ | |
| 146 | 4-$CH_3$ | H | 4-$CF_3$ | H | $C_2H_5$ | $-N(CH_3)_2$ | |
| 147 | 4-F | H | 4-t-Bu | H | n-Pr | $-N(CH_3)_2$ | |
| 148 | 4-F | H | 4-$CF_3$ | H | n-Pr | $-N(CH_3)_2$ | |
| 149 | 4-Cl | H | 4-t-Bu | H | n-Pr | $-N(CH_3)_2$ | |
| 150 | 4-Cl | H | 4-$CF_3$ | H | n-Pr | $-N(CH_3)_2$ | |
| 151 | 4-$CH_3$ | H | 4-t-Bu | H | n-Pr | $-N(CH_3)_2$ | |
| 152 | 4-$CH_3$ | H | 4-$CF_3$ | H | n-Pr | $-N(CH_3)_2$ | |
| 153 | 4-F | H | 4-t-Bu | H | iso-Pr | $-N(CH_3)_2$ | |
| 154 | 4-F | H | 4-$CF_3$ | H | iso-Pr | $-N(CH_3)_2$ | |
| 155 | 4-Cl | H | 4-t-Bu | H | iso-Pr | $-N(CH_3)_2$ | |
| 156 | 4-Cl | H | 4-$CF_3$ | H | iso-Pr | $-N(CH_3)_2$ | |
| 157 | 4-$CH_3$ | H | 4-t-Bu | H | iso-Pr | $-N(CH_3)_2$ | |
| 158 | 4-$CH_3$ | H | 4-$CF_3$ | H | iso-Pr | $-N(CH_3)_2$ | |
| 159 | 4-F | H | 4-$C_2H_5$ | H | $CH_3$ | $-N(CH_3)_2$ | |
| 160 | 4-Cl | H | 4-$C_2H_5$ | H | $CH_3$ | $-N(CH_3)_2$ | |
| 161 | 4-$CH_3$ | H | 4-$C_2H_5$ | H | $CH_3$ | $-N(CH_3)_2$ | |
| 162 | 4-F | H | 4-n-Bu | H | $CH_3$ | $-N(CH_3)_2$ | |
| 163 | 4-Cl | H | 4-n-Bu | H | $CH_3$ | $-N(CH_3)_2$ | |
| 164 | 4-$CH_3$ | H | 4-n-Bu | H | $CH_3$ | $-N(CH_3)_2$ | |
| 165 | 4-F | H | 4-s-Bu | H | $CH_3$ | $-N(CH_3)_2$ | |
| 166 | 4-Cl | H | 4-s-Bu | H | $CH_3$ | $-N(CH_3)_2$ | |
| 167 | 4-$CH_3$ | H | 4-s-Bu | H | $CH_3$ | $-N(CH_3)_2$ | |
| 168 | 4-F | H | 4-n-Pr | H | $CH_3$ | $-N(CH_3)_2$ | |
| 169 | 4-Cl | H | 4-n-Pr | H | $CH_3$ | $-N(CH_3)_2$ | |
| 170 | 4-$CH_3$ | H | 4-n-Pr | H | $CH_3$ | $-N(CH_3)_2$ | |
| 171 | 4-F | H | 4-iso-Pr | H | $CH_3$ | $-N(CH_3)_2$ | |
| 172 | 4-$CH_3$ | H | 4-iso-Pr | H | $CH_3$ | $-N(CH_3)_2$ | |
| 173 | 4-F | H | 4-cyclo-Pr | H | $CH_3$ | $-N(CH_3)_2$ | |
| 174 | 4-Cl | H | 4-cyclo-Pr | H | $CH_3$ | $-N(CH_3)_2$ | |
| 175 | 4-$CH_3$ | H | 4-cyclo-Pr | H | $CH_3$ | $-N(CH_3)_2$ | |
| 176 | 4-F | H | 4-(2,2-dimethyl-propyl) | H | $CH_3$ | $-N(CH_3)_2$ | m.p. 113–114° C. |
| 177 | 4-Cl | H | 4-(2,2-dimethyl-propyl) | H | $CH_3$ | $-N(CH_3)_2$ | |
| 178 | 4-$CH_3$ | H | 4-(2,2-dimethyl-propyl) | H | $CH_3$ | $-N(CH_3)_2$ | |
| 179 | 3-F | H | 4-t-Bu | H | $CH_3$ | $-N(CH_3)_2$ | |
| 180 | 3-Cl | H | 4-t-Bu | H | $CH_3$ | $-N(CH_3)_2$ | |
| 181 | 3-$CH_3$ | H | 4-t-Bu | H | $CH_3$ | $-N(CH_3)_2$ | |
| 182 | 3-F | H | 4-$CF_3$ | H | $CH_3$ | $-N(CH_3)_2$ | |
| 183 | 3-Cl | H | 4-$CF_3$ | H | $CH_3$ | $-N(CH_3)_2$ | |
| 184 | 3-$CH_3$ | H | 4-$CF_3$ | H | $CH_3$ | $-N(CH_3)_2$ | |
| 185 | 4-$CH_3$ | H | 4-t-Bu | H | $CH_3$ | $-N(CH_3)_2$ | m.p. 105–106° C. |
| 186 | 4-Cl | H | 4-$CF_3$ | H | $CH_3$ | $-NH(CH_2)_3OCH_3$ | |
| 187 | 4-F | H | 4-$CF_3$ | H | $CH_3$ | $-NH(CH_2)_3OCH_3$ | |
| 188 | 4-Cl | H | 4-t-Bu | H | $CH_3$ | $-NH(CH_2)_3OCH_3$ | |
| 189 | 4-F | H | 4-t-Bu | H | $CH_3$ | $-NH(CH_2)_3OCH_3$ | |
| 190 | 4-$CH_3$ | H | 4-$CF_3$ | H | $CH_3$ | $-NH(CH_2)_3OCH_3$ | |
| 191 | 4-$CH_3$ | H | 4-t-Bu | H | $CH_3$ | $-NH(CH_2)_3OCH_3$ | |
| 192 | 4-F | H | 4-t-Bu | H | $CH_3$ | $-NH(CH_2)_3OCH_3$ | |
| 193 | 4-F | H | 4-t-Bu | H | $CH_3$ | $-NH-CH_2OCH_3$ | |
| 194 | 4-F | H | 4-$CF_3$ | H | $CH_3$ | $-NH-CH_2OCH_3$ | |
| 195 | 4-Cl | H | 4-Cl | H | $CH_3$ | $-N(CH_2)_4$ | |
| 196 | 4-Cl | H | 4-Cl | H | cyclo-Hex | $-N(CH_3)_2$ | |
| 197 | 4-Cl | H | 4-Cl | H | $OCH_3$ | $-N(CH_3)_2$ | |

TABLE 1-continued

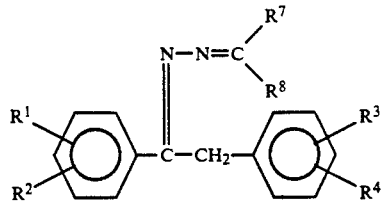
(I-1)

| Compound No. | $R^1$ | $R^2$ | $R^3$ | $R^4$ | $R^7$ | $R^8$ | Physical properties |
|---|---|---|---|---|---|---|---|
| 198 | 4-Cl | H | 4-Cl | H | $OC_2H_5$ | $-N(CH_3)_2$ | |
| 199 | 4-Cl | H | 4-Cl | H | cyclo-Pr | $-N(CH_3)_2$ | |

TABLE 2

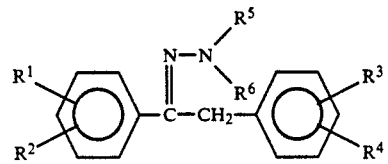
(I)

| Compound No. | $R^1$ | $R^2$ | $R^3$ | $R^4$ | $R^5$ | $R^6$ | Physical properties |
|---|---|---|---|---|---|---|---|
| 200 | 4-Cl | H | 4-Cl | H | H | —CNH—⟨⟩—CF₃ (‖O) | m.p. 194–198° C. |
| 201 | 4-Cl | H | 4-Cl | H | H | $-CO_2CH_3$ | m.p. 156–159° C. |
| 202 | 4-$OCHF_2$ | H | 4-F | H | H | $-CO_2C_2H_5$ | m.p. 119–119.5° C. |
| 203 | 4-Cl | H | 2-Cl | H | H | H | $n_D^{18.0} 1.6342$ |
| 204 | 4-Cl | H | 4-Cl | H | H | $CH_3$ | |
| 205 | 4-Cl | H | 4-Cl | H | H | $-COCH_3$ | |
| 206 | 4-Cl | H | 4-Cl | H | H | $-SO_2CH_3$ | |
| 207 | 4-Cl | H | 4-Cl | H | H | $-CH=CH_2$ | |
| 208 | 4-Cl | H | 4-Cl | H | H | $-C\equiv CH$ | |
| 209 | 4-Cl | H | 4-Cl | H | H | 2-pyridyl | |
| 210 | 4-Cl | H | 4-$CF_3$ | H | H | $-CO_2C_2H_5$ | m.p. 132–134° C. |
| 211 | H | H | 4-$CF_3$ | H | H | $-CO_2C_2H_5$ | m.p. 143–145° C. |
| 212 | 4-Cl | H | 4-t-Bu | H | H | $-COCH_3$ | m.p. 150–152° C. |
| 213 | 4-Br | H | 4-$CF_3$ | H | H | $-CO_2C_2H_5$ | m.p. 124–126° C. |
| 214 | 4-F | H | 4-Br | H | $CH_3$ | $-CO_2C_2H_5$ | $n_D^{35.6} 1.5754$ |
| 215 | 4-$CF_3$ | H | 4-$CF_3$ | H | H | $-CO_2C_2H_5$ | m.p. 129–131° C. |
| 216 | 4-$CF_3$ | H | 4-t-Bu | H | H | $-CO_2C_2H_5$ | m.p. 145° C. |
| 217 | 4-F | H | 4-t-Bu | H | H | $-CO_2C_3H_7$ | |
| 218 | 4-F | H | 4-Br | H | H | $-CO_2C_2H_5$ | |
| 219 | 4-F | H | 4-t-Bu | H | H | $-COC_2H_5$ | |
| 220 | 4-F | H | 4-Br | H | H | $-COCH_3$ | |
| 221 | 4-$CF_3$ | H | 4-$CF_3$ | H | H | $-CO_2C_2H_5$ | m.p. 123–125° C. |
| 222 | 4-F | H | 4-t-Bu | H | H | $-CO_2C_2H_5$ | m.p. 133–134° C. |
| 223 | 4-F | H | 4-t-Bu | H | H | $-COCH_3$ | m.p. 132–134° C. |
| 224 | 4-$CF_3$ | H | 4-F | H | H | $-CO_2C_2H_5$ | m.p. 120–121° C. |
| 225 | 4-F | H | 4-$CF_3$ | H | H | $-CO_2C_2H_5$ | m.p. 128–130° C. |
| 226 | 4-Cl | H | 4-t-Bu | H | H | $-CO_2C_2H_5$ | |
| 227 | 4-$CH_3$ | H | 4-t-Bu | H | H | $-CO_2C_2H_5$ | m.p. 129–130° C. |
| 228 | 4-$CH_3$ | H | 4-$CF_3$ | H | H | $-CO_2C_2H_5$ | |
| 229 | 4-F | H | 4-t-Bu | H | H | $-CO_2CH_3$ | |
| 230 | 4-F | H | 4-$CF_3$ | H | H | $-CO_2CH_3$ | |
| 231 | 4-Cl | H | 4-t-Bu | H | H | $-CO_2CH_3$ | |
| 232 | 4-Cl | H | 4-$CF_3$ | H | H | $-CO_2CH_3$ | |
| 233 | 4-$CH_3$ | H | 4-t-Bu | H | H | $-CO_2CH_3$ | |

TABLE 2-continued

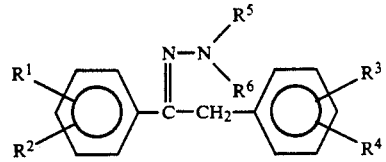
(I)

| Compound No. | $R^1$ | $R^2$ | $R^3$ | $R^4$ | $R^5$ | $R^6$ | Physical properties |
|---|---|---|---|---|---|---|---|
| 234 | 4-CH$_3$ | H | 4-CF$_3$ | H | H | —CO$_2$CH$_3$ | |
| 235 | 4-F | H | 4-CF$_3$ | H | H | —COCH$_3$ | |
| 236 | 4-Cl | H | 4-CF$_3$ | H | H | —COCH$_3$ | |
| 237 | 4-CH$_3$ | H | 4-t-Bu | H | H | —COCH$_3$ | |
| 238 | 4-CH$_3$ | H | 4-CF$_3$ | H | H | —COCH$_3$ | |
| 239 | 4-F | H | 4-t-Bu | H | CH$_3$ | —CO$_2$C$_2$H$_5$ | |
| 240 | 4-F | H | 4-CF$_3$ | H | CH$_3$ | —CO$_2$C$_2$H$_5$ | |
| 241 | 4-Cl | H | 4-t-Bu | H | CH$_3$ | —CO$_2$C$_2$H$_5$ | |
| 242 | 4-Cl | H | 4-CF$_3$ | H | CH$_3$ | —CO$_2$C$_2$H$_5$ | |
| 243 | 4-CH$_3$ | H | 4-t-Bu | H | CH$_3$ | —CO$_2$C$_2$H$_5$ | |
| 244 | 4-CH$_3$ | H | 4-CF$_3$ | H | CH$_3$ | —CO$_2$C$_2$H$_5$ | |
| 245 | 4-F | H | 4-t-Bu | H | H | —CHO | |
| 246 | 4-F | H | 4-CF$_3$ | H | H | —CHO | |
| 247 | 4-Cl | H | 4-t-Bu | H | H | —CHO | |
| 248 | 4-Cl | H | 4-CF$_3$ | H | H | —CHO | |
| 249 | 4-CH$_3$ | H | 4-t-Bu | H | H | —CHO | |
| 250 | 4-CH$_3$ | H | 4-CF$_3$ | H | H | —CHO | |
| 251 | 4-Cl | H | 4-OCH$_3$ | H | H | —CO$_2$CH$_3$ | |
| 252 | 4-Cl | H | 4-OSO$_2$CF$_3$ | H | H | —CO$_2$CH$_3$ | |
| 253 | 4-Cl | H | 4-SCF$_3$ | H | H | —CO$_2$CH$_3$ | |
| 254 | 4-Cl | H | 4-SO$_2$CH$_3$ | H | H | —CO$_2$CH$_3$ | |
| 255 | 4-Cl | H | 4-COOH | H | H | —CO$_2$CH$_3$ | |
| 256 | 4-Cl | H | 4-NHSO$_2$CH$_3$ | H | H | —CO$_2$CH$_3$ | |
| 257 | 4-Cl | H | 4-OCOCH$_3$ | H | H | —CO$_2$CH$_3$ | |
| 258 | 4-Cl | H | 4-OPO(OCH$_3$)$_2$ | H | H | —CO$_2$CH$_3$ | |
| 259 | 4-Cl | H | H | 4-O–(2-Cl,4-CF$_3$-phenyl) | H | —CO$_2$CH$_3$ | |
| 260 | 4-Cl | H | 4-OCOOC$_2$H$_5$ | H | H | —CO$_2$CH$_3$ | |
| 261 | 4-Cl | H | 4-COCH$_3$ | H | H | —CO$_2$CH$_3$ | |
| 262 | 4-Cl | H | 4–(4-Cl-phenyl) | H | H | —CO$_2$CH$_3$ | |
| 263 | 4-Cl | H | 4-cyclo-Pr | H | H | —CO$_2$CH$_3$ | |
| 264 | 4-Cl | H | 4-Cl | H | H | H.HCl | |
| 265 | 4-F | H | 4-CF$_3$ | H | H | H.HCl | |
| 266 | 4-F | H | 4-t-Bu | H | H | H.HCl | |
| 267 | 4-Cl | H | 4-CF$_3$ | H | H | H.HCl | |

Now, typical examples of the compound of the formula (IX), which are outside the scope of the compound of the formula (I), will be given in Table 3.

The compound of the formula (II-5) is an intermediate useful for the production of the compounds of the formulas (I) and (IX) and it is considered to be novel compound. Typical examples of these compounds will be given in the following Table 4.

TABLE 3

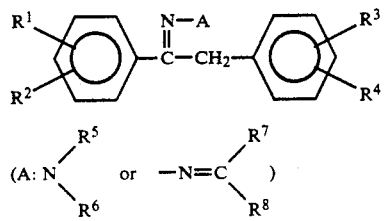
(IX')

TABLE 3-continued $A: -N\begin{smallmatrix}R^5\\R^6\end{smallmatrix}$  $A: -N=C\begin{smallmatrix}R^7\\R^8\end{smallmatrix}$

| Compound No. | $R^1$ | $R^2$ | $R^3$ | $R^4$ | $R^5$ | $R^6$ | $R^7$ | $R^8$ | Physical properties |
|---|---|---|---|---|---|---|---|---|---|
| 301 | 4-Cl | H | 4-NO$_2$ | H | | | CH$_3$ | —N(CH$_3$)$_2$ | m.p. 112–115° C. |
| 302 | 4-NO$_2$ | 3-OH | 4-CN | H | | | cyclo-Hex | —N(CH$_3$)$_2$ | |
| 303 | H | H | 4-NO$_2$ | H | | | CH$_3$ | —N(CH$_3$)$_2$ | |
| 304 | 4-OCH$_3$ | H | 4-F | H | H | —CO$_2$C$_2$H$_5$ | | | m.p. 130–131° C. |
| 305 | H | H | 4-t-Bu | H | H | —CO$_2$C$_2$H$_5$ | | | |
| 306 | 4-F | H | 4-t-Bu | H | H | —CONH$_2$ | | | |
| 307 | 4-F | H | 4-CF$_3$ | H | H | —CONH$_2$ | | | |
| 308 | 4-Cl | H | 4-t-Bu | H | H | —CONH$_2$ | | | |
| 309 | 4-Cl | H | 4-CF$_3$ | H | H | —CONH$_2$ | | | |
| 310 | 4-CH$_3$ | H | 4-CF$_3$ | H | H | —CONH$_2$ | | | |
| 311 | H | H | 4-F | H | iso-Pr | H | | | |
| 312 | H | H | 4-F | H | iso-Pr | —COCH$_3$ | | | |
| 313 | H | H | 4-Cl | H | H | H | | | |
| 314 | H | H | 4-Cl | H | | | Ph | 4-Cl | |
| 315 | H | H | 4-CH$_3$ | H | | | Ph | 4-CH$_3$ | |
| 316 | 3-OCH$_3$ | 4-OCH$_3$ | 4-OCH$_3$ | H | CH$_3$ | CH$_3$ | | | |
| 317 | 4-F | H | H | H | H | 4-methylphenyl sulfonyl | | | |
| 318 | 4-OCH$_3$ | H | 2-CH$_3$ | H | H | 4-methylphenyl sulfonyl | | | |

TABLE 4

$R^{12}$-phenyl(R$^{13}$)-C(=O)-CH$_2$-phenyl(R$^{14}$, R$^{15}$) (II-5)

| Intermediate No. | $R^{12}$ | $R^{13}$ | $R^{14}$ | $R^{15}$ | Physical properties |
|---|---|---|---|---|---|
| 1 | 4-Cl | H | 4-CF$_3$ | H | m.p. 117–119° C. |
| 2 | 4-F | H | 4-CF$_3$ | H | m.p. 87–89° C. |
| 3 | 4-Cl | H | 4-t-Bu | H | |
| 4 | 4-F | H | 4-t-Bu | H | m.p. 69–71° C. |
| 5 | 4-CF$_3$ | H | 4-Cl | H | |
| 6 | 4-Cl | H | 3-Cl | 4-CF$_3$ | |
| 7 | 4-Cl | H | 2-Cl | 4-CF$_3$ | |
| 8 | 4-Cl | H | 3-CF$_3$ | H | |
| 9 | 4-C$_2$H$_5$ | H | 4-CF$_3$ | H | m.p. 140–142° C. |
| 10 | 4-CH$_3$ | H | 4-CF$_3$ | H | m.p. 137–139° C. |
| 11 | 3-Cl | 4-Cl | 4-CF$_3$ | H | $n_D^{18.1}$ 1.5573 |
| 12 | 4-Br | H | 4-CF$_3$ | H | |
| 13 | 4-t-Bu | H | 4-t-Bu | H | |
| 14 | 4-CF$_3$ | H | 4-t-Bu | H | m.p. 88–89° C. |
| 15 | 4-CF$_3$ | H | 4-F | H | m.p. 78–81° C. |
| 16 | 4-t-Bu | H | 4-F | H | |
| 17 | 4-CF$_3$ | H | 4-CH$_3$ | H | |
| 18 | 3-F | 4-F | 4-t-Bu | H | m.p. 45–46° C. |
| 19 | 4-F | H | 4-(1,1-dimethyl)propyl | H | |
| 20 | 4-F | H | 4-t-Bu | 3-F | |
| 21 | 4-F | H | 4-CF$_3$ | 3-F | |
| 22 | 4-F | H | 3-t-Bu | H | |
| 23 | 4-F | H | 3-CF$_3$ | H | |
| 24 | 4-CH$_3$ | H | 3-t-Bu | H | |
| 25 | 4-CH$_3$ | H | 3-CF$_3$ | H | |
| 26 | 4-F | H | 4-t-Bu | 3-Cl | |
| 27 | 4-F | H | 4-CF$_3$ | 3-Cl | |
| 28 | 4-Cl | H | 4-t-Bu | 3-Cl | |
| 29 | 4-CH$_3$ | H | 4-t-Bu | 3-Cl | |
| 30 | 4-CH$_3$ | H | 4-CF$_3$ | 3-Cl | |
| 31 | 4-F | 3-F | 4-CF$_3$ | H | |
| 32 | 4-Cl | 3-F | 4-t-Bu | H | |
| 33 | 4-Cl | 3-F | 4-CF$_3$ | H | |
| 34 | 4-CH$_3$ | 3-F | 4-t-Bu | H | |
| 35 | 4-CH$_3$ | 3-F | 4-CF$_3$ | H | |
| 36 | 4-F | 3-Cl | 4-t-Bu | H | |
| 37 | 4-F | 3-Cl | 4-CF$_3$ | H | |
| 38 | 4-Cl | 3-Cl | 4-t-Bu | H | |
| 39 | 4-CH$_3$ | 3-Cl | 4-t-Bu | H | |
| 40 | 4-CH$_3$ | 3-Cl | 4-CF$_3$ | H | |
| 41 | 4-CH$_3$ | H | 4-t-Bu | H | |
| 42 | 4-F | H | 4-n-Bu | H | |
| 43 | 4-Cl | H | 4-n-Bu | H | |
| 44 | 4-CH$_3$ | H | 4-n-Bu | H | |
| 45 | 4-F | H | 4-s-Bu | H | |
| 46 | 4-Cl | H | 4-s-Bu | H | |
| 47 | 4-CH$_3$ | H | 4-s-Bu | H | |
| 48 | 4-F | H | 4-(2,2-dimethyl)propyl | H | |
| 49 | 4-Cl | H | 4-(2,2-dimethyl)propyl | H | |
| 50 | 4-CH$_3$ | H | 4-(2,2-dimethyl)propyl | H | |
| 51 | 3-F | H | 4-t-Bu | H | |
| 52 | 3-Cl | H | 4-t-Bu | H | |
| 53 | 3-CH$_3$ | H | 4-t-Bu | H | |
| 54 | 3-F | H | 4-CF$_3$ | H | |
| 55 | 3-Cl | H | 4-CF$_3$ | H | |
| 56 | 3-CH$_3$ | H | 4-CF$_3$ | H | |

In Tables 1 to 4, Ph represents a phenyl group; t-Bu, n-Bu and s-Bu represent tertiary, normal and secondary butyl groups, respectively; iso-Pr and n-Pr represent iso and normal propyl groups, respectively; and cyclo-Pr and cyclo-Hex represent cyclopropyl and cyclohexyl groups, respectively. Further, numerals before substituents indicate the position of the substituents, for example, 4-Cl for $R^1$ in Compound No. 1 indicates that Cl is located at the 4 position on the benzene ring. Compound No. 221 is a geometrical isomer of Compound No. 215.

The compounds of the formulas (I) and (IX) of the present invention exhibit excellent pesticidal activities as active ingredients for pesticides. For instance, they are effective against plant parasitic mites such as two-spotted spider mite (*Tetranychus urticae*), carmine spider mite (*Tetranychus cinnabarinus*) or citrus red mite (*Panonychus citri*) or bulb mite (*Rhizoglyphus echinopus*); agricultural insect pests such as diamondback moth (*Plutella xylostella*), cabbage armyworm (*Mamestra brassicae*), common cutworm (*Spodoptera litura*), rice leafroller (*Cnaphalocrocis medinalis*), *Adoxophyes* sp., colorado potato beetle (*Leptinotarsa decemlineata*), codling moth (*Laspeyresia pomonella*), bollworm (*Heliothis zea*), tobacco budworm (*Heliothis virescens*), boll weevil (*Anthonomus grandis*), gypsy moth (*Lymantria dispar*), cucurbit leaf beetle (*Aulacophora femoralis*), aphids, planthoppers, leafhoppers, scales, bugs, whiteflies, thrips, grasshoppers, anthomyiid flies, scarabs, black cutworm (*Agrotis ipsilon*), cutworm (*Agrotis segetum*) or ants; hygienic insect pests such as tropical rat mite (*Ornithonyssus bacoti*), cockroaches, housefly (*Musca domestica*) or house mosquito (*Culex pipiens pallens*); stored grain insect pests such as angoumois grain moth (*Sitotroga cerealella*), azuki bean weevil (*Callosobruchus chinensis*), confused flour beetle (*Tribolium confusum*) or mealworms; household goods insect pests such a casemaking clothes moth (*Tinea pellionella*), black carpet beetle (*Anthrenus scrophularidae*) or subterranean termites; and other parasites on domestic animals such as fleas, lice or flies. Further, they are also effective against plant parasitic nematodes such as root-knot nematodes, cyst nematodes, root-lesion nematodes, rice white-trip nematode (*Aphelenchoides besseyi*), straw berry bud nematode (*Nothotylenechus acris*) or pine wood nematode (*Bursaphelenchus liqnicolus*). Furthermore, they are also effective against the soil pests. The soil pests in the present invention are gastropods such as slugs or snails, or isopods such as pillbugs or sowbugs. The compounds of the present invention exhibit particularly excellent pesticidal activities against *Lepidoptera* pests and *Coleoptera* pests among the above mentioned various pests. Further, they are effective also against insect pests such as diamondback moth and housefly having the resistance to organophosphorus and pyrethroid insecticides. Furthermore, the compounds of the present invention have systemic properties. Therefore, by their application to soil treatment, it is possible to control not only noxious insects, mites, nematodes, gastropods and isopods in soil but also foliage pests. The compounds of the present invention are highly safe to mammals, fishes and useful insects and thus suitable for use s pesticides.

To use as active ingredients for pesticides, the compounds of the present invention may be formulated together with agricultural adjuvants into various forms such as dusts, granules, wettable powders, water dispersible granules, suspension concentrates, emulsifiable concentrates, aerosols or pastes, just like conventional agricultural chemicals.

Such formulations are usually composed of 0.1–90 parts by weight, preferably 0.5–90 parts by weight, more preferably 0.5–80 parts by weight, of active ingredient and 10–99.9 parts by weight, preferably 10–99.5 parts by weight, more preferably 20–99.5 parts by weight, of agricultural adjuvants. When such formulations are to be actually used, they may be used as they are or after being diluted with suitable diluents such as water to a predetermined concentration.

As the agricultural adjuvants, there may be mentioned carriers, emulsifiers, suspending agents, dispersants, extenders, penetrating agents, wetting agents, thickeners, defoaming agents, stabilizers and anti-freezing agents. They may be added as the case requires. The carriers may be divided into solid carriers and liquid carriers. As the solid carriers, there may be mentioned powders of animal and plant origin, such as starch, activated carbon, soybean flour, wheat flour, wood powder, fish powder or powdered milk; mineral powders such as talc, kaolin, bentonite, calcium carbonate, zeolite, diatomaceous earth, white carbon, clay or alumina; sulfur powder; or anhydrous sodium salfate. As the liquid carriers, there may be mentioned water; alcohols such as methyl alcohol or ethylene glycol; ketones such as acetone, methyl ethyl ketone or N-methyl-2-pyrrolidone; ethers such as dioxane or tetrahydrofuran; aliphatic hydrocarbons such as kerosene; aromatic hydrocarbons such as xylene, trimethylbenzene, tetramethylbenzene, cyclohexane or solvent naphtha; halogenated hydrocarbons such as chloroform or chlorobenzene; acid amides such as dimethylformamide; esters such as ethyl acetate or glycerine ester of a fatty acid; nitriles such as acetonitrile; sulfur-containing compounds such as dimethyl sulfoxide; or vegetable oils such as soybean oil or corn oil.

Now, Formulation Examples of pesticides containing the compounds of the present invention as active ingredients, will be described. However, the compounds as active ingredients, the types of agricultural adjuvants, the blend ratios or the types of the formulations are not restricted to these specific Examples.

FORMULATION EXAMPLE 1

| (1) Compound No. 9 | 20 parts by weight |
|---|---|
| (2) Kaoline | 52 parts by weight |
| (3) Sodium lignin sulfonate | 8 parts by weight |
| (4) White carbon | 20 parts by weight |

The above components are uniformly mixed to obtain a wettable powder.

FORMULATION EXAMPLE 2

| (1) Compound No. 32 | 5 parts by weight |
|---|---|
| (2) Talc | 95 parts by weight |

The above components are uniformly mixed to obtain a dust.

FORMULATION EXAMPLE 3

| (1) Compound No. 210 | 20 parts by weight |
|---|---|
| (2) N-methyl-2-pyrrolidone | 10 parts by weight |
| (3) Polyoxyethylenealkylphenyl ether | 10 parts by weight |
| (4) Xylene | 60 parts by weight |

The above components are uniformly mixed and dissolved to obtain an emulsifiable concentrate.

FORMULATION EXAMPLE 4

| (1) Kaoline | 83 parts by weight |
|---|---|
| (2) Sodium lignin sulfonate | 2 parts by weight |
| (3) Polyoxyethylenealkylaryl sulfate | 5 parts by weight |
| (4) Fine silica powder | 10 parts by weight |

A mixture of the above components is mixed with compound No. 38 in a weight ratio of 4:1 to obtain a wettable powder.

FORMULATION EXAMPLE 5

| (1) Compound No. 42 | 40 parts by weight |
|---|---|
| (2) Oxylated polyalkylphenol phosphate-triethanolamine | 2 parts by weight |
| (3) Silicone | 0.2 part by weight |
| (4) Xanthane gum | 0.1 part by weight |
| (5) Ethylene glycol | 5 parts by weight |
| (6) Water | 52.7 parts by weight |

The above components are uniformly mixed and pulverized to obtain an water based suspension concentrate.

FORMULATION EXAMPLE 6

| (1) Compound No. 60 | 75 parts by weight |
|---|---|
| (2) Sodium polycarboxylate | 13.5 parts by weight |
| (3) Anhydrous sodium sulfate | 10 parts by weight |
| (4) Dextrine | 0.5 part by weight |
| (5) Sodium alkylsulfonate | 1 part by weight |

The above components are introduced in a high speed mixing pulverizer, and 20% of water is added thereto, and the mixture are granulated and dried to obtain a water dispersible granule.

FORMULATION EXAMPLE 7

| (1) Compound No. 32 | 5 parts by weight |
|---|---|
| (2) Bentonite | 33 parts by weight |
| (3) Kaoline | 57 parts by weight |
| (4) Sodium lignin sulfonate | 5 parts by weight |

To the above components, a suitable amount of water for granulation is added, and the mixture is mixed and granulated to obtain a granule.

FORMULATION EXAMPLE 8

| (1) Compound No. 9 | 2.5 parts by weight |
|---|---|
| (2) N-methyl-2-pyrrolidone | 2.5 parts by weight |
| (3) Soybean oil | 95.0 parts by weight |

The above components are uniformly mixed and dissolved to obtain an ultra low volume formulation.

FORMULATION EXAMPLE 9

| (1) Compound No. 60 | 5 parts by weight |
|---|---|
| (2) N-methyl-2-pyrrolidone | 5 parts by weight |
| (3) Polyoxyethylenealkylaryl ether | 10 parts by weight |
| (4) Xylene | 80 parts by weight |

The above components are uniformly mixed to obtain an emulsifiable concentrate.

FORMULATION EXAMPLE 10

| (1) Compound No. 38 | 10 parts by weight |
|---|---|
| (2) Corn oil | 77 parts by weight |
| (3) Polyoxyethylene hardened castor oil | 12 parts by weight |
| (4) Organic bentonite | 1 part by weight |

The above components are uniformly mixed and pulverized to obtain an oil based suspension concentrate.

Further, the pesticides containing the compounds of the present invention as active ingredients may be used in admixture with or in combination with other agricultural chemicals such as insecticides, miticides, nematicides, fungicides, antiviral agents, attractants, herbicides or plant growth regulators, as the case requires. In some cases, the effectiveness will be improved by such combination.

For instance, as such insecticides, miticides or nematicides, there may be mentioned organophosphorus compounds such as O-(4-bromo-2-chlorophenyl) O-ethyl S-propyl phosphorothioate, O-(2,2-dichlorovinyl) O,O-dimethyl phosphate, O-ethyl O-[3-methyl-4-(methylthio)phenyl] N-isopropylphosphoramidate, O,O-dimethyl O-(4-nitro-m-tolyl) phosphorothioate, O-ethyl O-(4-nitrophenyl) phenylphosphonothioate, O,O-diethyl O-(2-isopropyl-6-methylpyrimidin-4-yl) phosphorothioate, O,O-dimethyl O-(3,5,6-trichloro-2-pyridyl) phosphorothioate, O,S-dimethyl N-acetylphosphoramidothioate, O-(2,4-dichlorophenyl) O-ethyl S-propyl phosphorodithioate or (RS)-S-sec-butyl O-ethyl 2-oxo-1,3-thiazolydin-3-yl phosphonothioate; carbamate compounds such as 1-naphthyl N-methylcarbamate, 2-isopropoxyphenyl N-methylcarbamate, 2-methyl-2-(methylthio)propionaldehyde O-methylcarbamoyloxime, 2,3-dihydro-2,2-dimethylbenzofuran-7-yl N-methylcarbamate, dimethyl N,N'-[thiobis[(methylimino)carbonyloxy]] bisethanimidothioate, S-methyl N-(methylcarbamoyloxy) thioacetoimidate, N,N-dimethyl-2-methylcarbamoyloxyimino-2-(methylthio)acetamide, 2-(ethylthiomethyl)phenyl N-methylcarbamate, 2-dimethylamino-5,6-dimethylpyrimidin-4-yl N,N-dimethylcarbamate or 2-sec-butylphenyl-N-methylcarbamate; nereistoxin derivatives such as S,S'-2-dimethyl aminotrimethylene bis(thiocarbamate) or N,N-dimethyl-1,2,3-trithian-5-yl amine; organic chlorine compounds such as 2,2,2-trichloro-1,1-bis(4-chlorophenyl)ethanol or 4-chlorophenyl-2,4,5-trichlorophenyl sulfone; organic metal compounds such as bis[tris(2 methyl-2-phenylpropyl)tin]oxide; pyrethroid compounds such as (RS)-α-cyano-3-phenoxybenzyl (RS)-2-(4-chlorophenyl)-3-methylbutyrate, 3-phenoxybenzyl (1RS)-cis,trans-3-(2,2-dichlorovinyl)-2,2-dimethylcyclopropanecarboxylate, (RS)-α-cyano-3-phenoxybenzyl (1R)-cis,trans-3-(2,2-dichlorovinyl) 2,2-dimethylcyclopropanecarboxylate, (S)-α-cyano-3-phenoxybenzyl (1R)-cis-3-(2,2-dibromovinyl)-2,2-dimethylcyclopropanecarboxylate, (RS)-α-cyano-3-phenoxybenzyl (1RS)-cis,trans-3-(2-chloro-3,3,3-trifluoropropenyl)-2,2-dimethylcyclopropanecarboxylate, 4-methyl-2,3,5,6-tetrafluorobenzyl-3-(2-chloro-3,3,3-trifluoro-1-propenyl)-2,2-dimethylcyclopropane carboxylate or 2-(4-ethoxyphenyl)-2-methylpropyl 3-phenoxybenzyl ether (common name: ethofenprox; hereinafter referred to simply as Compound No. A-1); benzoyl urea compounds such as 1-(4-chlorophenyl)-3-(2,6-difluorobenzoyl)urea, 1-[3,5-dichloro-4-(3-chloro-5-trifluoromethyl-2-pyridyloxy)- phenyl]-3-(2,6-difluorobenzoyl)urea or 1-(3,5-dichloro-2,4-difluorophenyl)-3-(2,6-difluorobenzoyl)urea; juvenile hormone analogs such as isopropyl (2E,4E)-11-methoxy-3,7,11-trimethyl-2,4-dodecadienoate; pyridazinone compounds such as 2-tert-butyl-5-(4-tert-butylbenzylthio)-4-chloro-3(2H)-pyridazinone; pyrazole compounds such as tert-butyl 4-[(1,3-dimethyl-5-phenoxypyrazol-4-yl)methylene aminooxymethyl] benzoate; nitro compounds such as 1-(6-chloro-3-pyridylmethyl)-N-nitro-imidazolidin-2-ylideneamine (common name: imidacloprid; hereinafter referred to simply as Compound No. A-2), 1-[N-(6-chloro-3-pyridylmethyl)-N-ethylamino]-1-methylamino-2-nitroethylene (EP 302389A; hereinafter referred to simply as Compound No. A-3), 2-methylamino-2-[N-methyl-N-(6-chloro-3-pyridylmethyl)amino]-1-nitroethylene (EP 302389A; hereinafter referred to simply as Compound No. A-4), 1-(6-chloro-3-pyridylmethyl)amino-1-dimethylamino-2-nitroethylene (EP 302389A; hereinafter referred to simply as Compound No. A-5), 1-(6-chloro-3-pyridylmethyl)-2-(1-nitro-2-allylthioethylidene)imidazolidine (EP 437784A; hereinafter referred to simply as Compound No. A-6), 1-(6-chloro-3-pyridylmethyl)-2-(1-nitro-2-ethylthioethylidene)imidazolidine (EP 437784A; hereinafter referred to simply as Compound No. A-7), 1-(6-3-pyridylmethyl)-2-(1-nitro-2-β-methylallylthioethylidene)imidazolidine (EP 437784A; hereinafter referred to simply as Compound No. A-8), 1-(6-chloro-3-pyridylmethyl)-3-methyl-2-nitroguanidine (EP 383091A; hereinafter referred to simply as Compound No. A-9), 1-(6-chloro-3-pyridylmethyl)-3,3-dimethyl-2-nitroguanidine (EP 383091A; hereinafter referred to simply as Compound No. A-10), 3-(6-chloro-3-pyridylmethyl)-2-nitromethylene-thiazolidine (EP 192060A; hereinater referred to simply as Compound No. A-11), 1-(6-chloro-3-pyridylmethyl)-2-(nitromethylene)-imidazolidine (EP 163855A: hereinafter referred to simply as Compound No. A-12), 6-(6-chloro-3-pyridylmethylamino)-1,3-dimethyl-5-nitro-1,2,3,4-tetrahydropyrimidine (EP 366085A; hereinafter referred to simply a Compound No. A-13) or 1-(6-chloro-3-pyridylmethyl)-5-nitro-3-methyl-6-methylamino-1,2,3,4-tetrahydropyrimidine (EP 366085A; hereinafter referred to simply as Compound No. A-14); dinitro compounds; organic sulfur compounds; urea compounds; triazine compounds; hydrazine compounds; and other compounds such as 2-tert-butylimino-3-isopropyl-5-phenyl-3,4,5,6-tetrahydro-2H-1,3,5-thiadiazin-4 one (common name: buprofezin; hereinafter referred to simply as Compound No. A-15), trans-(4-chlorophenyl)-N-cyclohexyl-4-methyl-2-oxothiazolidinon-3-carboxamide, N-methylbis(2,4-xylyliminomethyl)amine, N'-(4-chloro-o-tolyl)-N,N-dimethylformamidine or (4-ethoxyphenyl)-[3-(4-fluoro-3-phenoxyphenyl)-propyl](dimethyl)silane (common name: silafluofen; hereinafter referred to simply as Compound No. A-16). Further, microbial insecticides such as *Bacillus thuringiensis* agent or nuclear polyhedrosis virus; antibiotics such as avermectin or milbemycin; or the like may also be used in admixture with or in combination with the pesticides of the present invention. Among these insecticides, miticides and nematicides, Compound Nos. A-1, A-2, A-3, A-4, A-5, A-6, A-7, A-8, A-9, A-10, A-11, A-12, A-13, A-14, A-15 and A-16 are preferred. More preferred are Compound Nos. A-1, A-2, A-3, A-6, A-15 and A-16. It is particularly preferred that at least one of Compound Nos. 9, 32, 38, 42, 60 and 210 of the present invention and at least one of Compound Nos. A-1, A-2, A-3, A-6, A-15 and A-16 are mixed, and the mixture is applied so that the former would be from 50 to 5,000 g/ha and the later would be from 10 to 5,000 g/ha, whereby excellent pesticidal effects will be obtained against insect pests such as diamondback moth (*Plutella xylostella*), rice leafroller (*Cnaphalocrocis medinalis*), *Adoxophyes* sp., planthoppers, leafhoppers and aphids.

As the fungicides, there may be mentioned organophosphorus compounds such as S-benzyl O,O-diisopropyl phosphorothioate, O-ethyl S,S-diphenyl phosphorodithioate or aluminium ethyl hydrogen phosphonate; organic chlorine compounds such as 4,5,6,7-tetrachlorophthalide or tetrachloroisophthalonitrile; dithiocarbamate compounds such as polymeric manganese ethylenebis(dithiocarbamate), polymeric zinc ethylenebis(dithiocarbamate), manganese ethylenebis(dithiocarbamate) complex with zinc salt, dizinc bis(dimethyldithiocarbamate)ethylenebis-(dithiocarbamate) or polymeric zinc propylenebis(dithiocarbamate); N-halogenothioalkyl compounds such as 3a,4,7,7a-tetrahydro-N-tetrahydro-N-(1,1,2,2-tetrachlroethylsulfenyl)-phthalimide or N-(trichloromethylsulfenyl)phthalimide; dicarboxy imide compounds such as 3-(3,5-dichlorophenyl)-N-isopropyl-2,4-dioxoimidazolidine-1-carboxamide, (RS)-3-(3,5-dichlorophenyl) -5-methyl-5-vinyl-1,3-oxazolidine-2,4-dione or N-(3,5-dichlorophenyl) -1,2-dimethylcyclopropane-1,2-dicarboximide; benzimidazole compounds such as methyl 1-(butylcarbamoyl)benzimidazol-2-yl-carbamate or dimethyl 4,4'-(o-phenylene)bis(3-thioallophanate); azole compounds such as 1-(4-chlorophenoxy)-3,3-dimethyl-1-(1H-1,2,4-triazol-1-yl)butanone, 1-(biphenyl-4-yloxy)-3,3-dimethyl-1-(1H-1,2,4-triazol-1-yl)butan-2-ol, 1-[N-(4-chloro-2-trifluoromethylphenyl) -2-propoxyacetoimidoyl]imidazole, 1-[2-(2,4-dichlorophenyl)-4-ethyl-1,3-dioxolan-2-ylmethyl]-1H-1,2,4-triazole, 1-[2-(2,4-dichlorophenyl)-4-propyl-1,3-dioxolan-2-ylmethyl]-1H-1,2,4-triazole or 1-[2-(2,4-dichlorophenyl)pentyl]-1H-1,2,4-triazole; carbinol compounds such as 2,4'-dichloro-α-(pyrimidin-5-yl)benzhydryl alcohol or (±)-2,4'-difluoro-α-(1H-1,2,4-triazol-1-ylmethyl)benzhydryl alcohol; benzanilide compounds such as 3'-isopropoxy-o-toluanilide or α, α, α-trifluoro-3'-isopropoxy-o-toluanilide; phenylamide compounds such as methyl N-(2-methoxyacetyl)-N-(2,6-xylyl)-DL-alaninate; pyridinamine compounds such as 3-chloro-N-(3-chloro-2,6-dinitro-4-α,α,α-trifluorotolyl)-5-trifluoromethyl-2-pyridinamine; piperazine compounds; morpholine compounds; anthraquinone compounds; quinoxaline compounds; crotonicacid compounds; sulfenic acid compounds; urea compounds and other compounds such as diisopropyl 1,3-dithiolan-2-ylidenemalonate, 5-methyl-1,2,4-triazolo[3,4-b]benzothiazole, 1,2,5,6-tetrahydropyrrolo[3,2,1-ij]quinolin-4-one, 6-(3,5-dichloro-4-methylphenyl)-3(2H)-pyridazinone, 3-allyloxy-1,2-benzisothiazole-1,1-dioxide or 1-(4-chlorobenzyl)-1-cyclopentyl-3-phenylurea. Further, antibiotic substances such as validamycin A may also be used in admixture with or in combination with the pesticides of the present invention.

The blend ratio of the compound of the present invention to other agricultural chemical is usually within a range of from 1:100 to 100:1, preferably from 1:50 to 50:1. The pesticide containing the compound of the present invention as active ingredient is applied in an active ingredient concentration of from 1 to 100,000 ppm, preferably from 1 to 50,000 ppm, more preferably from 10 to 20,000 ppm. The active ingredient concentration may optionally be changed depending upon the formulation, the manner, purpose, timing or place of the application and the abundance of the insect pests. For instance, aquatic noxious insects can be controlled by applying the formulation having the above-mentioned concentration to the site of the outbreak, and thus, the concentration of the active ingredient in water is less than the above-mentioned range.

The amount of the application of the active ingredient per unit surface area is usually from about 1 to 50,000 g, preferably from 10 to 10,000 g, more preferably from 50 to 5,000 g, per hectare. However, in a certain special case, the amount of the application may be outside the above range.

Various formulations containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a feed containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

TEST EXAMPLE 1

Insecticidal test against common cutworm (*Spodoptera litura*)

Each formulation containing an active ingredient was dispersed in water to obtain a dispersion containing the active ingredient at a concentration of 800 ppm. Leaves of cabbage were dipped in the dispersion for about 10 seconds and then dried in air. A sheet of moistened filter paper was placed in a Petri dish having a diameter of 9 cm, and the dried leaves of cabbage were put on the filter paper. Ten larvae of common cutworm (*Spodoptera litura*) in second or third instar were released on the leaves, and the Petri dish was covered and kept in a constant temperature chamber with lightening at a temperature of 26° C. On the 5th day after release, dead insects were counted, and the mortality was calculated in accordance with the following equation.

$$\text{Mortality (\%)} = \frac{\text{Number of dead insects}}{\text{Number of insects released}} \times 100$$

As the result, the mortality was 100% with each of Compound Nos. 1, 2, 4-12, 15, 17, 30-34, 36-39, 42, 43, 45, 47-49, 51, 53, 55-62, 74, 201, 202, 210-215, 221, 224, 225 and 303, and the mortality was 90% with each of Compounds Nos. 20, 65, 200 and 304.

TEST EXAMPLE 2

Insecticidal test against diamondback moth (*Putella xylostell*)

The test was conducted in the same manner as in Test Example 1 except that the common cutworm in second or third instar was changed to diamondback moth (*Plutella xylestella*) in second or third instar, and the mortality was calculated in the same manner. The mortality was 100% with each of Compounds Nos. 1, 2, 4, 5, 7-12, 30, 32, 34, 38, 39, 41-45, 49, 60, 61, 201, 202, 210, 213 and 301.

TEST EXAMPLE 3

Insecticidal test against rice leafroller (*Cnaphalocrocis medinalis*)

Each formulation containing an active ingredient was dispersed in water to obtain a dispersion containing the active ingredient at a concentration of 800 ppm. Leaves of corn were dipped in the dispersion for about 10 seconds and then dried in air. A sheet of moistened filter paper was placed in an ice cream cup having a diameter of 8 cm, and the dried leaves were put on the filter paper. Five larvae of rice leafroller *Cnaphalocrocis medinalis*) in second or third instar were released on the leaves, and the ice cream cup was covered and kept in constant temperature chamber with lightening at a temperature of 26° C. On the 5th day after release, dead insects were counted, and the mortality was calculated in the same manner as in Test Example 1.

The mortality was 100% with each of Compounds Nos. 9, 32-34, 38, 210 and 211.

TEST EXAMPLE 4

Insecticidal test against *Adoxophyes* sp.

Each formulation containing an active ingredient was dispersed in water to obtain a dispersion containing the active ingredient at a concentration of 800 ppm. A small piece of an artificial feed (tradename: Insecta LF ®, manufactured by Nippon Nosan Kogyo K.K.) was dipped in the dispersion for about 60 seconds and then left to stand at room temperature for about one hour. A sheet of filter paper was placed in an ice cream cup having a diameter of 8 cm, and the treated artificial feed was put on the filter paper. Ten larvae of *Adoxophyes* sp. in second or third instar were released thereon, and the ice cream cup was covered and kept in a constant temperature chamber with lightening at a temperature of 26° C. On the 8th or 9th day after release, dead insects were counted, and the mortality was calculated in the same manner as in Test Example 1.

The mortality was 100% with each of Compounds Nos. 9, 32, 38, 42, 60 and 210.

TEST EXAMPLE 5

Insecticidal test against cucurbit leaf beetle (*Aulacophora femoralis*)

Each formulation containing an active ingredient was dispersed in water to obtain a dispersion containing the active ingredient at a concentration of 800 ppm. Leaves of cucumber were dipped in the dispersion for about 10 seconds and then dried in air. A sheet of moistened filter paper was placed in an ice cream cup having a diameter of 8 cm, and the dried leaves were put on the filter paper. Five adults of cucurbit leaf beetle (*Aulacophora femoralis*) were released on the leaves, and the ice cream cup was covered and kept in a constant temperature chamber with lightening at a temperature of 26° C. On the 5th day after release, dead insects were counted, and the mortality was calculated in the same manner as in Test Example 1.

The mortality was 100% with Compound No. 9.

We claim:

1. A hydrazone compound of the formula (I) or its salt

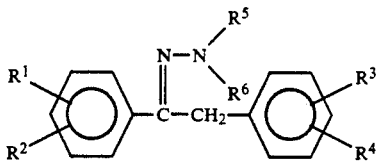
(I)

wherein each of $R^1$, $R^2$ and $R^4$, which are independent of one another, is a hydrogen atom, a halogen atom, an alkyl group which may be substituted by a halogen atom, or an alkoxy group which may be substituted by a halogen atom, $R^3$ is a halogen atom, an alkyl group which may be substituted by a halogen atom, or an alkoxy group which may be substituted by a halogen atom, $R^5$ is a hydrogen atom, or an alkyl group, $R^6$ is $X^7CO-$ (wherein $X^7$ is a hydrogen atom, or an alkyl group), or $X^8OCO-$ (wherein $X^8$ is an alkyl group), or $R^5$ and $R^6$ together form $=CR^7R^8$ (wherein $R^7$ is a hydrogen atom, or an alkyl group, and $R^8$ is an amino group which may be substituted by an alkyl group, or an alkoxy group), provided that the following cases (1) to (3) are excluded:

(1) a case where $R^2$, $R^4$ and $R^5$ are hydrogen atoms, $R^6$ is an ethoxycarbonyl group, and at least one of $R^1$ and $R^3$ is p-methoxy group, (2) a case where $R^1$, $R^2$, $R^4$ and $R^5$ are hydrogen atoms, $R^3$ is a p-tert-butyl group, and $R^6$ is an ethoxycarbonyl group, (3) a case where $R^1$, $R^2$ and $R^4$ are hydrogen atoms, $R^3$ is a p-fluorine atom, $R^5$ is an isopropyl group, and $R^6$ is an acetyl group.

2. The compound according to claim 1, which is [4'-chloro-2-(4-trifluoromethylphenyl)acetophenone] N'-[1-(dimethylamino)ethylidene]hydrazone, [4'-fluro-2-(4-trifluoromethylphenyl)acetophenone] N'-[1-(dimethylamino)ethylidene]hydrazone, ethyl 3-[1-(4-chlorophenyl-2-(4-trifluoromethylphenyl) ethylidene]-carbazate, [4'-chloro-2-(4-tert-butylphenyl)acetophenone] N'-[1-(dimethylamino)ethylidene]hydrazone, or [4'-fluoro-2-(4-tert-butylphenyl)acetophenone] N'-[1-(dimethylamino)ethylidene]hydrazone.

3. An insecticidal composition comprising an insecticidally effective amount of a hydrazone compound of claim 1, and an agricultural adjuvant.

4. An insecticidal method which comprises applying to insects an insecticidally effective amount of a hydrazone compound of claim 1.

* * * * *